United States Patent
Tan et al.

(10) Patent No.: US 6,207,146 B1
(45) Date of Patent: Mar. 27, 2001

(54) GENE EXPRESSION IN MAMMALIAN CELLS

(75) Inventors: Yin Hwee Tan; Wanjin Hong, both of Crescent (SG)

(73) Assignee: Institute of Molecular and Cell Biology, Singapore (SG)

( * ) Notice: Subject to any disclaimer, the term of this patent is extended or adjusted under 35 U.S.C. 154(b) by 0 days.

(21) Appl. No.: 08/913,778

(22) PCT Filed: Mar. 22, 1996

(86) PCT No.: PCT/CA96/00174

§ 371 Date: Oct. 24, 1997

§ 102(e) Date: Oct. 24, 1997

(87) PCT Pub. No.: WO96/30531

PCT Pub. Date: Oct. 3, 1996

(30) Foreign Application Priority Data

Mar. 24, 1995 (GB) .................................. 9506051

(51) Int. Cl.$^7$ .......................... A61K 38/21; C12N 15/09; C12N 15/63; C07H 21/04
(52) U.S. Cl. .................. 424/85.6; 435/69.4; 435/320.1; 435/325; 435/360; 530/350; 536/23.52; 536/24.1
(58) Field of Search .................... 424/85.6; 435/69.4, 435/320.1, 325, 360; 530/350; 536/23.52, 24.1

(56) References Cited

U.S. PATENT DOCUMENTS

| | | | |
|---|---|---|---|
| 4,954,437 | * | 9/1990 | Beck et al. ........................... 435/69.4 |
| 4,966,843 | | 10/1990 | McCormick et al. . |
| 5,089,397 | * | 2/1992 | Kushner et al. ...................... 435/69.1 |
| 5,376,567 | | 12/1994 | McCormick et al. . |
| 5,514,567 | | 5/1996 | Sugano et al. . |

FOREIGN PATENT DOCUMENTS

| | | |
|---|---|---|
| 00 028 033 | 2/1986 | (EP) . |
| 0 270 799 | 6/1988 | (EP) . |
| 287 075 | 10/1988 | (EP) . |
| 0 529 300 | 3/1993 | (EP) . |
| 0 551 535 | 7/1993 | (EP) . |
| 2 177 914 | 2/1987 | (GB) . |

OTHER PUBLICATIONS

Drug Research vol. 37, No. 1, Apr. 1987, pp. 482–485, XP000578037 W.Reiser et al: "Recombinant human interferon beta from mammalian cell lines" cited in the application see the whole document.

Database WPI Week 9130 Feb. 28, 1991 Derwent Publications Ltd., London, GB; AN 91215983 XP002010946 U. Kiessling et al: "Production of recombinant human growth hormone using mouse cells repeatedly co:transfected with expression vector and marker vector" & DD,A,287 531 (zent molekular ag), Feb. 28, 1991 see abstract.

Gene, vol. 76, No. 1, Mar. 15, 1989, Amsterdam NL, pp. 81–88, XP000008769 J. McNeall et al: "Hyperinducible gene expression from a metallothionein promoter containing additional metal–responsive elements".

Chen et al. Enhanced viral resistance in transgenic mice expressing the human beta 1 interferon. J. Virol. vol. 62(10):3883–3887, Oct. 1988.*

Asano et al. Interferon production under the control of heterlotous inducible enhancer and promoters. Microbiol. immunol. vol. 32(6):589–596, Jun. 1988.*

Hayashi et al. Effects of tumor promoters on the frequency of metallothionein I gene amplification in cells exposed to cadmium. Cancer Research vol. 43:5433–5436, Nov. 1983.*

* cited by examiner

Primary Examiner—Robert A. Schwartzman
Assistant Examiner—William Sandals
(74) Attorney, Agent, or Firm—Nixon & Vanderhye P.C.

(57) ABSTRACT

Proteins such as human β-interferon or human erythropoietin are prepared by culturing mammalian cells which harbour a nucleic acid sequence comprising: (i) a coding sequence which encodes the desired protein and which is operably linked to a promoter capable of directing expression of the coding sequence in a mammalian cell in the presence of a heavy metal ion; and (ii) a first selectable marker sequence comprises a metallothionein gene and which is operably linked to a promoter capable of directing expression of the metallothionein gene in a mammalian cell in the presence of a heavy metal ion; and optionally (iii) a second selectable marker sequence which comprises a neo gene and which is operably linked to a promoter capable of directing expression of the neo gene in a mammalian cell.

3 Claims, 12 Drawing Sheets

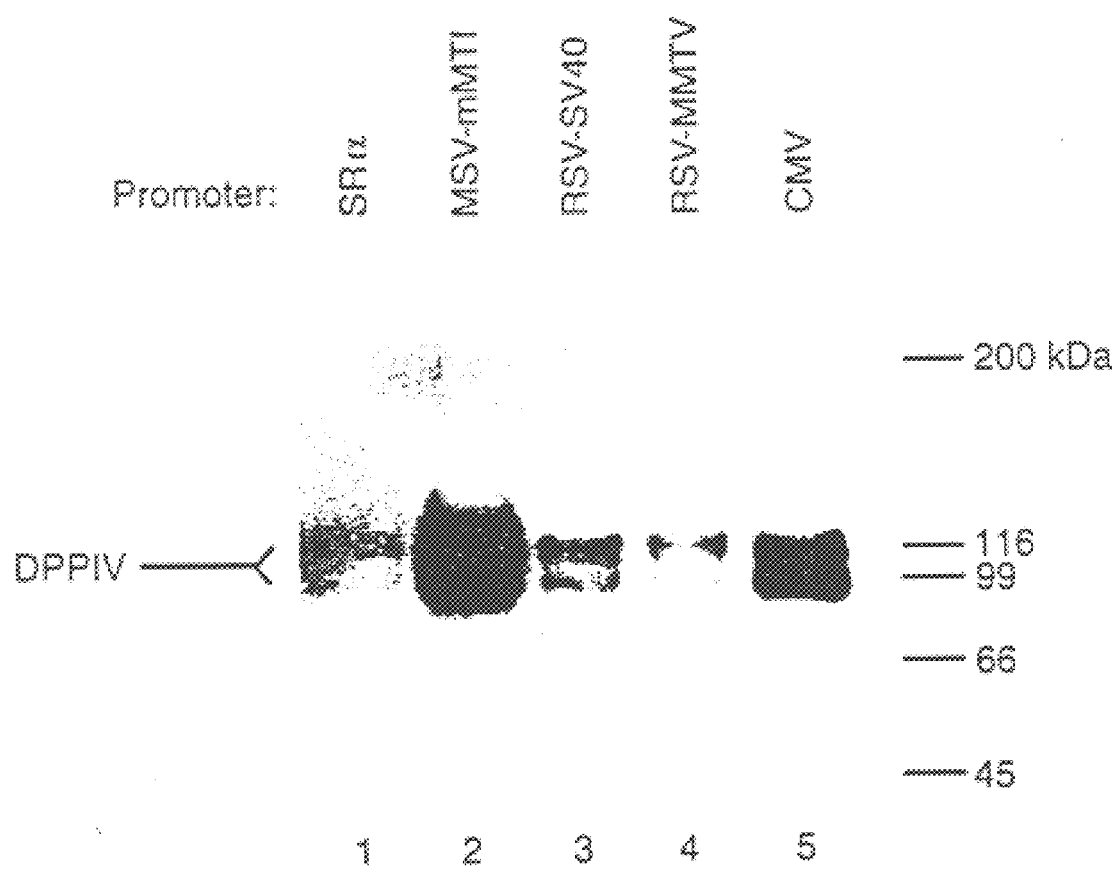

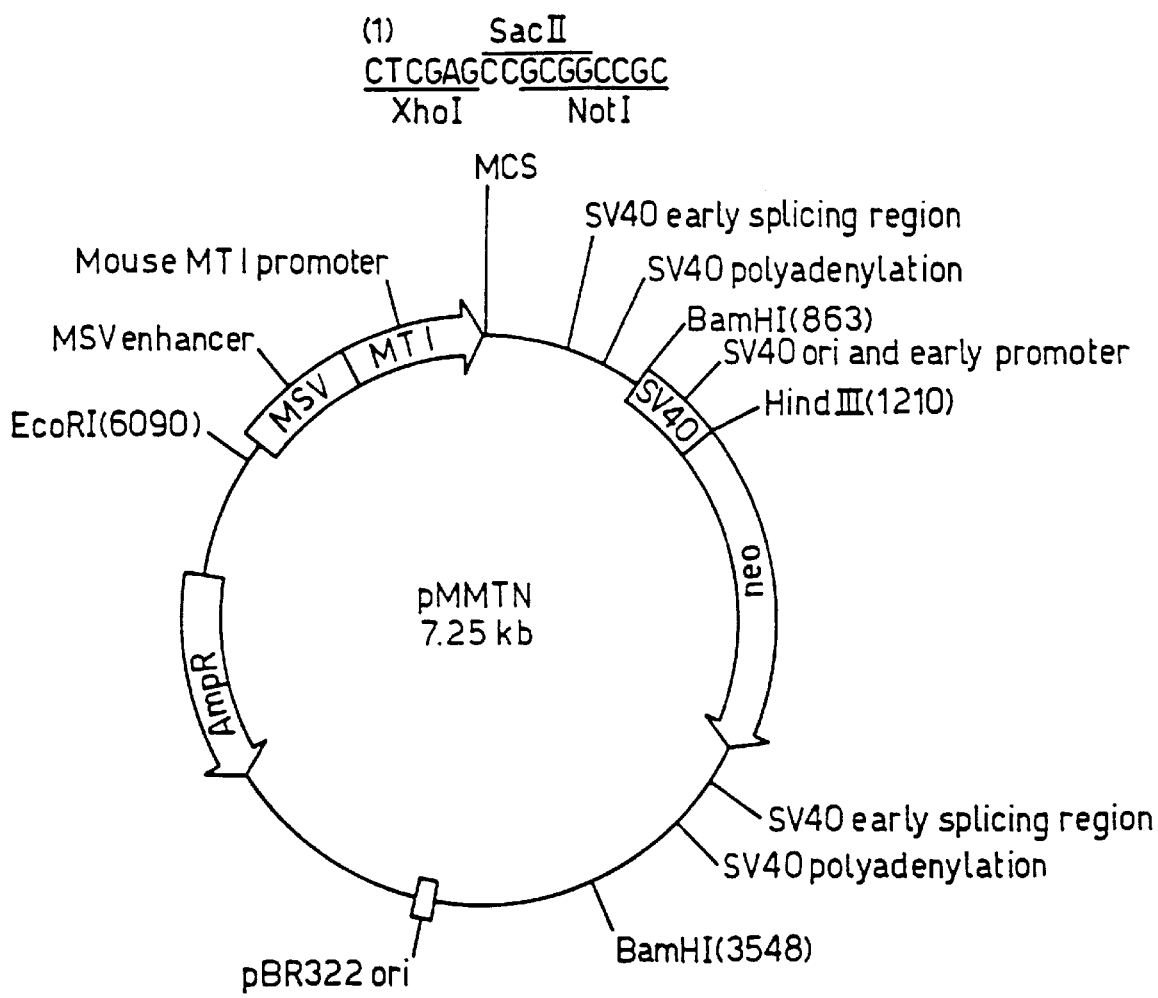

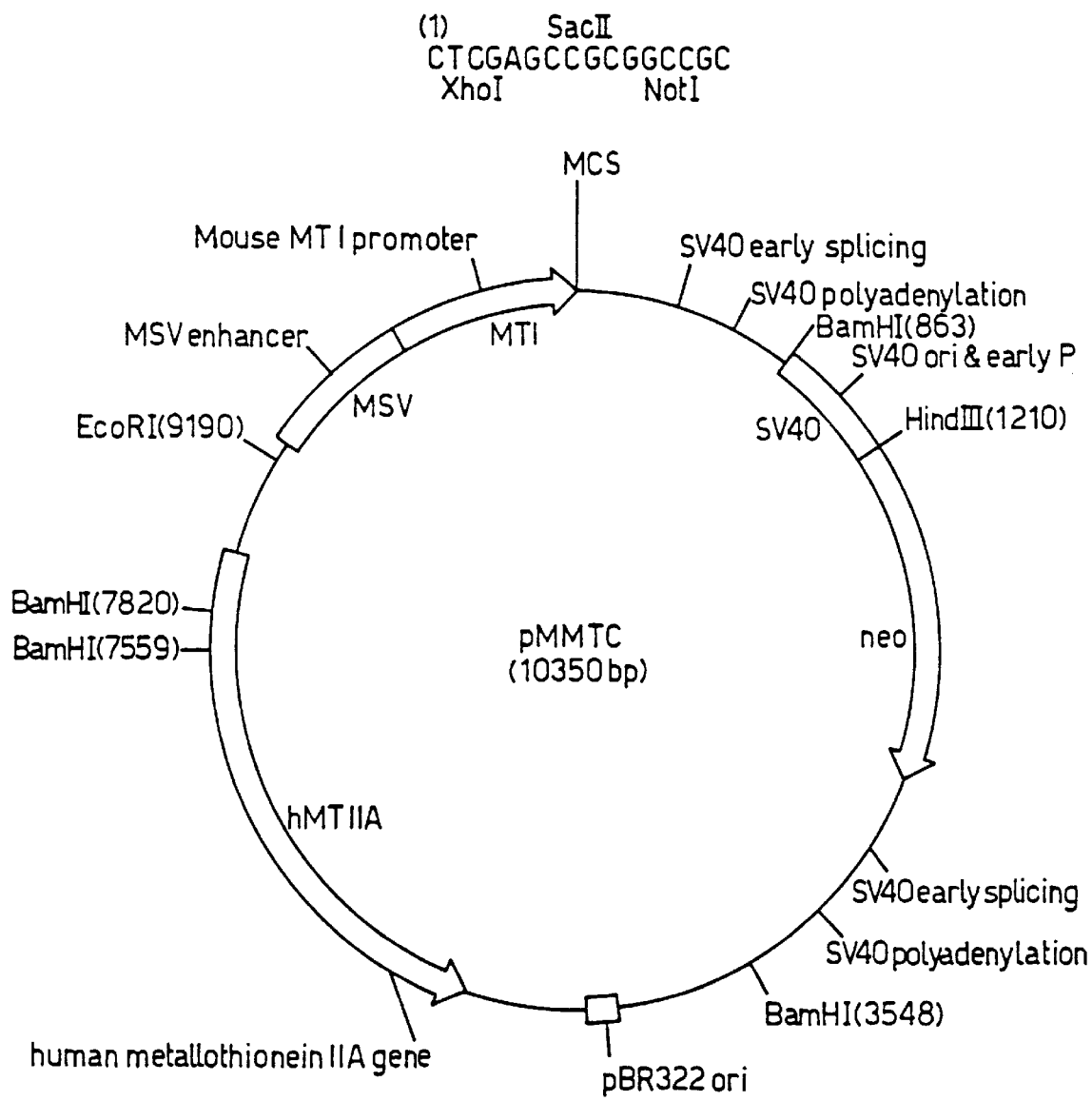

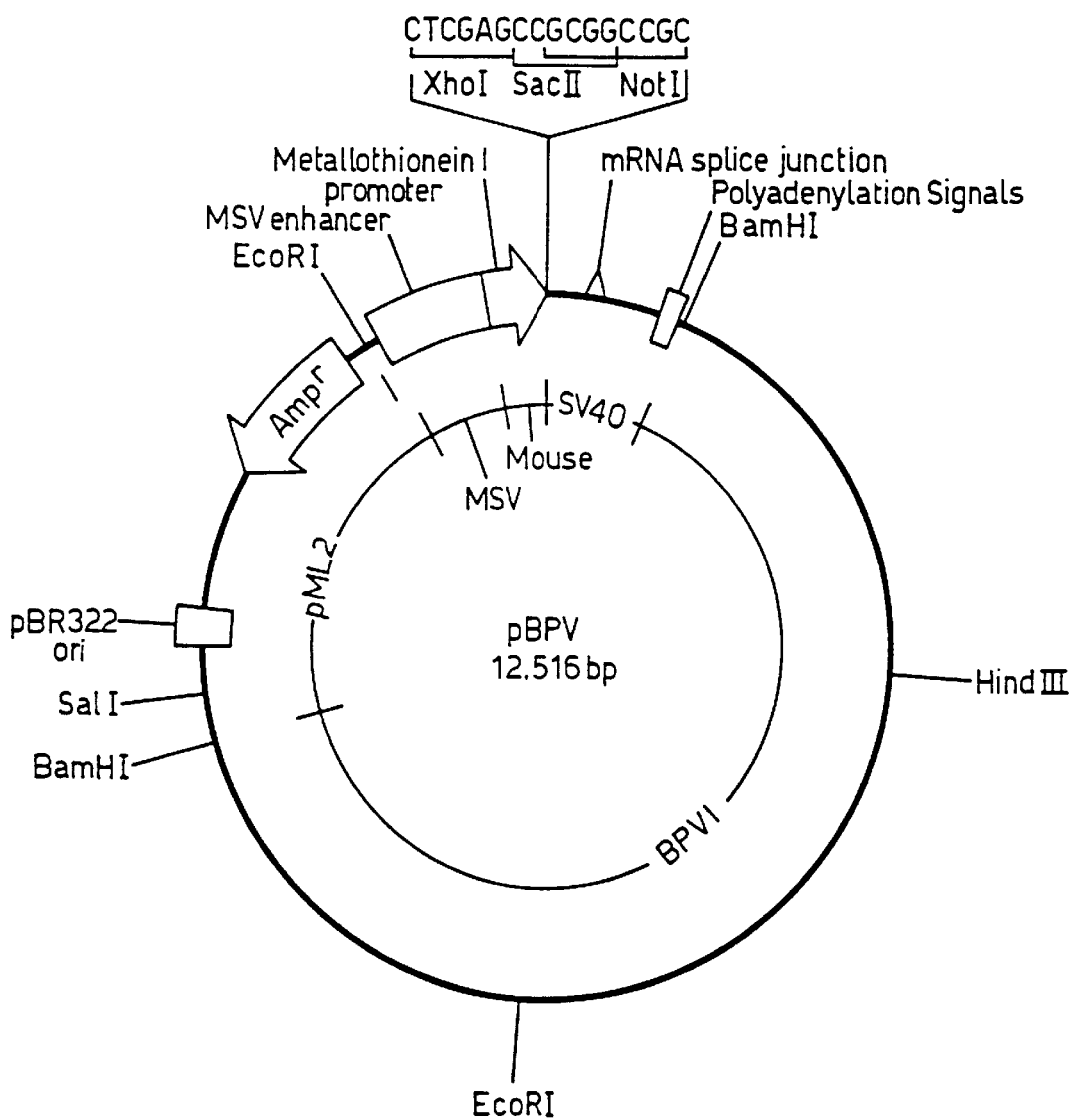

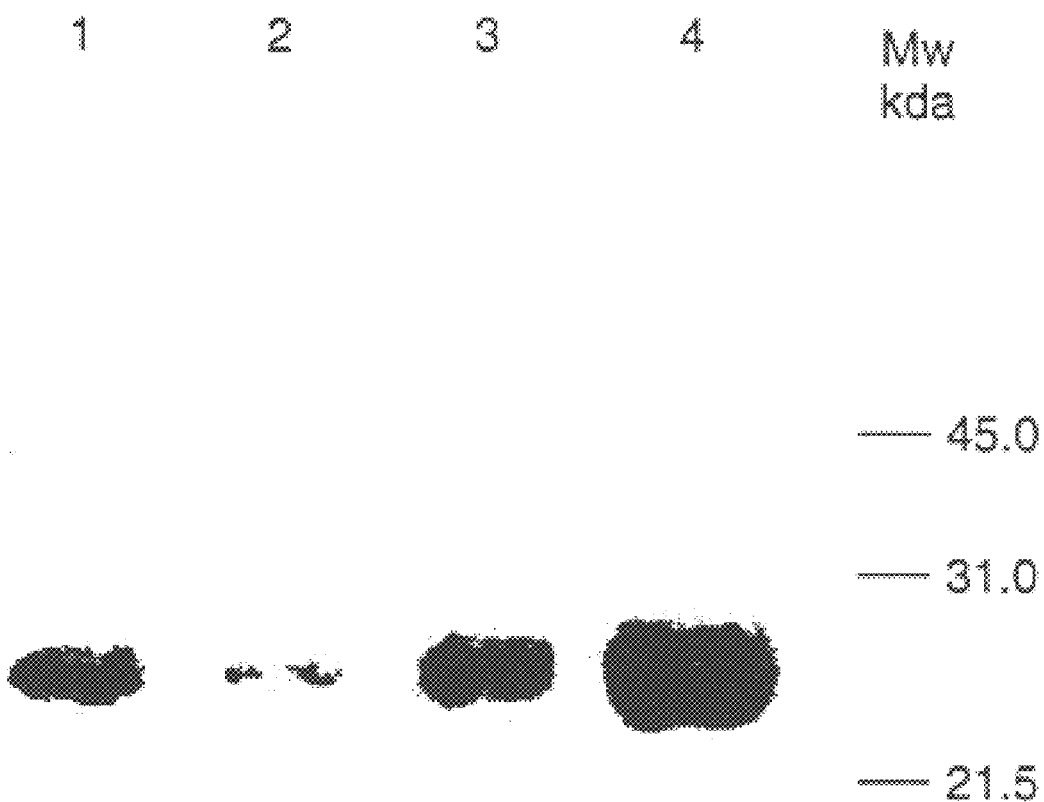

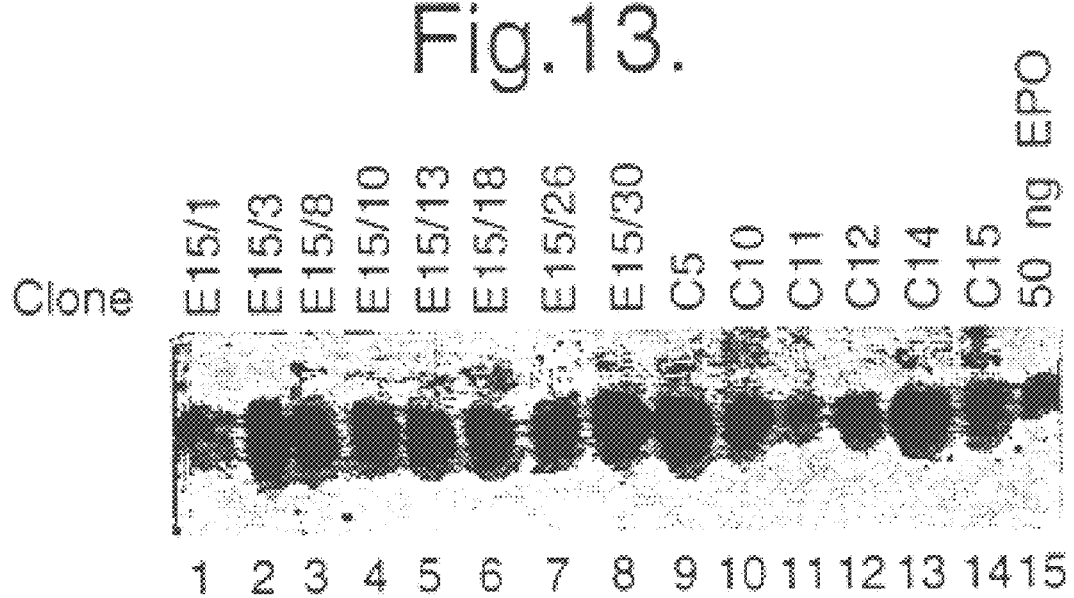

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 23 base pairs
      (B) TYPE: nucleic acid
      (C) STRANDEDNESS: double
      (D) TOPOLOGY: circular (ii) MOLECULE TYPE: other nucleic acid
      (A) DESCRIPTION:  /desc = "Multiple cloning site of
          plasmid pBPV"

(xi) SEQUENCE DESCRIPTION: SEQ ID NO: 1:

CTCGAGCCGC GGCCGCTTCG AGG                                     23

(2) INFORMATION FOR SEQ ID NO: 2:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: other nucleic acid
      (A) DESCRIPTION:   /desc = "PCR primer"

(xi) SEQUENCE DESCRIPTION: SEQ ID NO: 2:

GGGGTACCAT GACCAACAAG TGTCTCCTC                                                29

(2) INFORMATION FOR SEQ ID NO: 3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO: 3:

GGAATTCTTC AGTTTCGGAG GTAACCTGT                                                29

(2) INFORMATION FOR SEQ ID NO: 4:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO: 4:

GTGGATCCGC CGCCACCATG GGGGTGCACG AATGTCCTGC CTG                                 43

(2) INFORMATION FOR SEQ ID NO: 5:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer fragment"

(xi) SEQUENCE DESCRIPTION: SEQ ID NO: 5:

CCGCCGCCAC C                                                                   11

(2) INFORMATION FOR SEQ ID NO: 6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO: 6:

GATCTAGACA GTTCTTGTCA ATGAGGTTGA AG                                             32

(2) INFORMATION FOR SEQ ID NO: 7:

(i) SEQUENCE CHARACTERISTICS:
        (A) LENGTH: 16 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "Fragment of multiple cloning site of plasmid pBPV"

(xi) SEQUENCE DESCRIPTION: SEQ ID NO: 7:

CTCGAGCCGC GGCCGC                                                                                              16

GENE EXPRESSION IN MAMMALIAN CELLS

This invention relates to the expression of genes in mammalian cells, particularly genes responsible for proteins whose biological activity in vivo is affected by a diversity of factors including specific glycosylation. Examples of such genes are the human β-interferon (IFNβ), human erythropoietin (EPO), human chorionic gonadotropin, various other cytokines and growth factors as well as specific viral antigens such as Dengue viral proteins whose structure may be relevant for the development of vaccines.

Previously, genes have been extensively expressed in mammalian cell lines, particularly in mutant Chinese Hamster Ovary (CHO) cells deficient in the dihydrofolate reductase gene (dhfr) as devised by the method of Urlaub et al, PNAS U.S.A. 77, 4216–4220, 1980. A variety of expression systems have been used. Many vectors for the expression of genes in such cells are therefore available. Typically, the selection procedures used to isolate cells transformed with the expression vectors rely on using methotrexate to select for transformants in which both the dhfr and the target genes are coamplified.

The dhfr gene, which enables cells to withstand methotrexate, is usually incorporated in the vector with the gene whose expression is desired. Selection of cells under increasing concentrations of methotrexate is then performed. This leads to amplification of the number of dhfr genes present in each cell of the population, as cells with higher copy numbers withstand greater concentrations of methotrexate. As the dhfr gene is amplified, the copy number of the gene of interest increases concomitantly with the copy number of the dhfr gene, so that increased expression of the gene of interest is achieved.

Unfortunately, these amplified genes have been reported to be variably unstable in the absence of continued selection (Schimke, J. Biol. Chem. 263, 5989–5992, 1988). This instability is inherent to the presently available expression systems of CHO dhfr⁻ cells.

For many years, several promoters have been used to drive the expression of the target genes such as the SV40 early promoter, the CMV early promoter and the SRα promoter. The CMV and SRα promoters are claimed to be the strongest (Wenger et al, Anal. Biochem. 221, 416–418, 1994).

In one report, the β-interferon promoter has also been used to drive the expression of the β-interferon gene in the mutant CHO dhfr⁻ cells (U.S. Pat. No. 5,376,567). In this system, however, the selected CHO dhfr⁻ cells had to be superinduced by the method of Tan et al (Tan et al, PNAS U.S.A. 67, 464–471, 1970; Tan et al, U.S. Pat. No. 3,773, 924) to effect a higher level of β-interferon production. In this system a significant percentage of the superinduced β-interferon produced by the CHO dhfr⁻ cells was not glycosylated.

The mouse metallothionein gene (mMT1) promoter has also been used for the expression of β-interferon genes in CHO cells, BHK and LTK⁻ mouse cells (Reiser et al 1987 Drug Res. 37, 4, 482–485). However, the expression of β-interferon with this promoter was not as good as the SV40 early promoter in CHO cells. Further, β-interferon expression from these cells mediated by the mMT1 promoter was inducible by heavy metals. Heavy metals are however extremely toxic to the cells and this system was therefore abandoned. Instead, Reiser et al used the CHO dhfr⁻ expression system in conjunction with the SV40 early promoter (Reiser et al, Drug Res. 37,4, 482–485 (1987) and EP-A-0529300) to produce β-interferon in CHO dhfr⁻ cells as derived by the method of Urlaub et al (1980).

We have now expressed β-interferon in wild-type CHO cells. Wild-type CHO cells were transfected with a vector comprising a β-interferon gene under the control of a mouse sarcoma viral enhancer and mouse metallothionein promoter (MSV-mMT1), a neo gene under the control of promoter capable of driving expression of the neo gene in both *E. coli* and mammalian cells and a human metallothionein gene having its own promoter. Transfected cells capable of expressing β-interferon were selected by first exposing cells to geneticin (antibiotic G418) and thus eliminating cells lacking the neo gene and then exposing the surviving cells to increasing concentrations of a heavy metal ion.

The heavy metal ion enhanced the MSV-mMT1 promoter for the β-interferon gene, thus increasing β-interferon expression. The heavy metal ion also induced the human metallothionein gene promoter, causing expression of human metallothionein. The human metallothionein protected the cells against the toxic effect of the heavy metal ion. The presence of the heavy metal ion ensured that there was continual selection of cells which had the transfecting vector, or at least the β-interferon gene and the human metallothionein gene and their respective promoters, integrated into their genome.

The selected cells that had been successfully transfected expressed β-interferon. Expression was surprisingly improved when the cells were cultured in the presence of $Zn^{2+}$. The β-interferon had improved properties, in particular a higher bioavailability, than prior β-interferons.

These findings have general applicability. Accordingly, the present invention provides:

a nucleic acid vector comprising:

| | |
|---|---|
| (i) | a coding sequence which encodes a protein of interest and which is operably linked to a promoter capable of directing expression of the coding sequence in a mammalian cell in the presence of a heavy metal ion; |
| (ii) | a first selectable marker sequence which comprises a metallothionein gene and which is operably linked to a promoter capable of directing expression of the metallothionein gene in a mammalian cell in the presence of a heavy metal ion; and |
| (iii) | a second selectable marker sequence which comprises a neo gene and which is operably linked to a promoter capable of directing expression of the neo gene in a mammalian cell; | mammalian cells which harbour a nucleic acid sequence comprising:

| | |
|---|---|
| (i) | a coding sequence which encodes a protein of interest and which is operably linked to a promoter capable of directing expression of the coding sequence in a mammalian cell in the presence of a heavy metal ion; |
| (ii) | a first selectable marker sequence which comprises a metallothionein gene and which is operably linked to a promoter capable of directing expression of the metallothionein gene in a mammalian cell in the presence of a heavy metal ion; and optionally |
| (iii) | a second selectable marker sequence which comprises a neo gene and which is operably linked to a promoter capable of directing |

-continued expression of the neo gene in a mammalian cell;

a process for producing such cells, which process comprises (a) transfecting mammalian cells with a vector of the invention;
(b) exposing the transfected cells to geneticin to eliminate thereby cells lacking the neo gene; and
(c) exposing the cells that survive step (a) to progressively increasing concentrations of a heavy metal ion to select thereby the desired cells.

use of a neo gene and a metallothionein gene as selectable marker genes in a single vector; and a process for the preparation of a protein of interest, which process comprising culturing mammalian cells of the invention under conditions allowing expression of the desired protein and recovering the desired protein thus expressed.

By using both a neo gene and a metallothionein gene as selectable markers in a single vector, it is possible to select for transformed mammalian cells, such as wild-type CHO cells, which have multiple copies of the expression vector stably integrated into their genomes. This selection system therefore facilitates the preparation and identification of stably transformed mammalian cells such as the wild-type CHO cells and avoids the need for dhfr⁻ cells. The transformed cells enable the stable expression of genes such as the human β-interferon gene because they have multiple copies, typically at least 20–100 copies or more, of these genes integrated into their genomes.

Moreover, the use of relatively high concentrations of $Cd^{2+}$ (up to 200 $\mu$M) in the selection procedure eliminates inadvertent microbial contaminants such as mycoplasma that may become associated with the transfected cells during tissue culture procedures. Thus, the present invention minimises the possibility of microbial contamination of transfected cells.

Further, one particular promoter/enhancer system according to the invention surprisingly gave a significantly higher level of expression than the strong promoter systems that have been used in the past. This promoter/enhancer is the MSV-mMT1 system which comprises the promoter of the mouse metallothionein gene 1 (mMT1) flanked upstream with a mouse sarcoma virus (MSV) enhancer.

A promoter of a metallothionein gene, particularly the combined MSV-mMT1 promoter/enhancer system, can be operably linked to a gene of interest such as the human β-interferon gene or the human erythropoietin gene. A vector comprising such an arrangement can give a high level of expression of the gene product in wild-type CHO cells. Therefore, the inventors have identified a new and unexpectedly powerful expression system suitable for use in mammalian cells, particularly wild type mammalian cells. Products, such as human β-interferon and human erythropoietin, may be expressed with unexpected/novel biological properties such as higher bio-availability. Such properties may result in higher efficacy/additional utility for the product.

It is therefore possible according to the invention to express genes such as a β-interferon gene and others in large quantities in wild-type mammalian cells such as wild-type CHO cells and to do so in a stable manner, without the need for continuing selection and dependence on the CHO dhfr⁻-methotrexate selection system. The invention can be applied to a large variety of mammalian cells. In this way, it enables the expression of appropriate target genes with a glycosylation pattern and a cellular environment unique to the cell type used.

A vector according to the invention is an expression vector. It comprises three sequences that are expressible in mammalian cells. Thus a vector of the invention comprises:

(i) a coding sequence comprising a gene of interest whose expression is desired, for example the human β-interferon gene;
(ii) a first selectable marker sequence comprising a metallothionein gene which confers resistance to heavy metal ions, such as cadmium, copper and zinc, on mammalian cells expressing the gene of interest; and
(iii) a second selectable marker sequence comprising a neo gene which confers resistance to the antibiotic kanamycin upon transformed bacterial cells expressing the gene and resistance to the geneticin (antibiotic G418) upon mammalian cells expressing the gene.

Each of these three sequences will typically be associated with other elements that control their expression. In relation to each sequence, the following elements are generally present, usually in a 5' to 3' arrangement: a promoter for directing expression of the sequence and optionally a regulator of the promoter, a translational start codon, the coding/marker sequence, a polyadenylation signal and a transcriptional terminator. Further, the coding sequence and/or either or both of the marker sequences may optionally be operably linked to an enhancer that increases the expression obtained under the control of the promoter. Suitable enhancers include the Rous Sarcoma Virus (RSV) enhancer and the Mouse Sarcoma Virus (MSV) enhancer.

Further, a vector according to the invention will typically comprise one or more origins of replication, for example a bacterial origin of replication, such as the pBR322 origin, that allows replication in bacterial cells. Alternatively or additionally, one or more eukaryotic origins of replication may be included in the vector so that replication is possible in, for example yeast cells and/or mammalian cells.

The vector may also comprise one or more introns or other non-coding sequences 3' or 5' to the coding sequence or to one or more of the marker sequences. Such non-coding sequences may be derived from any organism, or may be synthetic in nature. Thus, they may have any sequence. Such sequences may be included if they enhance or do not impair correct expression of the coding sequence or marker sequences.

In vectors of the invention, the coding sequence and the marker sequences are each operably linked to a promoter capable of directing their expression in a mammalian cell. Optionally, one or more of these promoters may also be capable of directing expression in other cells, for example non-mammalian eukaryotic cells, such as yeast cells or insect cells and/or prokaryotic cells. "Operably linked" refers to a juxtaposition wherein the promoter and the coding/marker sequence are in a relationship permitting the coding/marker sequence to be expressed under the control of the promoter. Thus, there may be elements such as 5' non-coding sequence between the promoter and coding/marker sequence. Such sequences can be included in the construct if they enhance or do not impair the correct control of the coding/marker sequence by the promoter.

Any promoter capable of enhancing expression in a mammalian cell in the presence of a heavy metal ion such as $Cd^{2-}$, $Cu^{2-}$ and $Zn^{2+}$ may be operably linked to the coding sequence. A suitable promoter is a metallothionein gene promoter. The mouse metallothionein gene I (MMT1) promoter is preferred.

Suitable promoter/enhancer combinations for the encoding sequence include the mTM1 promoter flanked upstream with MSV enhancer (MSV-mMT1) and the combination of the RSV enhancer and the MMTV promoter. MSV-mMT1 is preferred.

Similarly, any promoter capable of enhancing expression in a mammalian cell in the presence of a heavy metal ion such as $Cd^{2+}$, $Cu^{2+}$ and $Zn^{2+}$ may be operably linked to the metallothionein gene such as a human metallothionein gene. Preferably, the marker sequence gene is a human metallothionein gene, such as the human metallothionein gene IIA, which has its own promoter.

The second selectable marker sequence is a neo gene. More than one type of this gene exists in nature: any specific neo gene can be used in a vector of the invention. One preferred neo gene is the *E. coli* neo gene.

The promoter for the neo gene is capable of directing expression of the gene in a mammalian cell. Suitable promoters are the cytomegalovirus (CMV) early promoter, the SV40 promoter, the mouse mammary tumour virus promoter, the human elongation factor 1 α-P promoter (EF-1α-P), the SRα promoter and a metallothionein gene promoter such as mMT1. The promoter may also be capable of expressing the neo gene in bacteria such as *E. coli* in which a vector of the invention may be constructed.

Whilst the protection against antibiotics conferred by the neo gene is qualitative in the sense that once expressed neo gene will confer antibiotic resistance on a cell, the protection against heavy metals conferred by the metallothionein gene is quantitative. The greater the level of expression of the metallothionein gene in a cell the greater the cell's resistance is to heavy metals. Thus, cells having a high copy number of metallothionein genes will be expected to have a high resistance to heavy metals.

Therefore, cells including many copies of a vector of the invention have a higher resistance to heavy metals than cells comprising one or a few copies. Accordingly, it is possible to select for transfected cells having high copy numbers of a vector of the invention (and therefore high copy numbers of the coding sequence for a gene such as human β-interferon) by progressively increasing the concentration of heavy metals to which the cells are exposed. Thus, cells having progressively higher copy numbers of the vector according to the invention are selected.

Therefore, the combination of selectable markers found in the vectors of the invention allows a two stage selection process for transfected cells of interest. First, cells are exposed to geneticin (antiobiotic G418) which eliminates cells lacking the neo gene and therefore lacking the vector of the invention altogether. The neo gene serves no further function after this step.

Second, selection is effected with progressively increasing levels of heavy metal ions, which selects cells having multiple copies of the vectors, especially cells having multiple copies integrated into their genomes. In this selection process, cells that survive high concentrations of heavy metal ions express metallothionein to a high degree, for example because they include a large number of vectors of the invention and/or because the vector or vectors that have integrated into their genome are in a chromosomal location that encourages strong expression.

Any suitable heavy metal ions may be used. Thus, any heavy metal ion that is toxic to cells of the invention and to which an expressed metallothionein gene confers protection may be used. For example, zinc ions ($Zn^{2-}$), copper ions ($Cu^{2-}$) or preferably cadmium ions ($Cd^{2+}$) may be used. Concentrations of a heavy metal ion of from 5 to 100, indeed up to 200, $\mu M$ may be applied to effect selection. A concentration of from 130 to 170 $\mu M$, preferably about 150 $\mu M$ $Zn^{2-}$, is suitable.

In order to effect selection using heavy metal ions, these ions may be provided as salts, in combination with any suitable counterion such as sulphate or chloride.

Because selected cells are resistant to the toxicity of heavy metals which, as it happens, are inducers of the promoter for the coding sequence, the expression of the protein of interest can be maximised by heavy metal ions such as 130 to 170 $\mu M$ $Zn^{2-}$ which are inducers of the promoter.

In addition to the neo and metallothionein genes, the vector may also contain one or more further selectable marker genes, for example an ampicillin resistance gene for the identification of bacterial transformants.

In the vectors of the invention, the nucleic acid may be DNA or RNA, preferably DNA. The vectors may be expression vectors of any type. The vector must of course be compatible with the mammalian cell which it is going to transfect. The vector may be in linear or circular form. For example, the vector may be a plasmid vector, typically a DNA plasmid. A preferred plasmid vector is pMMTC (Example 2; FIG. 3).

Those of skill in the art will be able to prepare suitable vectors starting with widely available vectors which will be modified by genetic engineering techniques such as those described by Sambrook et al (Molecular Cloning: A Laboratory Manual: 1999). So far as plasmid vectors are concerned, a suitable starting vector is the plasmid pRSN (Low et al (1991): JBC 266; 19710–19716), which is widely available. A further suitable plasmid starting vector is pBR322.

Vectors of the invention may be able to effect integration of some or all of their nucleic acid sequence into a host cell genome or they may remain free in the host cell. Integrative vectors are preferred. This is because they give stable expression of coding sequences such as that of the human β-interferon gene.

The transfected mammalian cells may be BHK, COS, VERO, human fibroblastoid such as ClO, HeLa, or human lymphoblastoid cells or cells of a human tumour cell line. Preferably, however, the cells are CHO cells, particularly wild-type CHO cells.

Desirably, transfected cells will have all or part of a vector of the invention integrated into their genomes. Such cells are preferred because they give stable expression of the coding sequence contained in the vector. Preferably, one or more copies of the entire vector will be integrated, with cells having multiple integrated copies of the vector, for example from 20 to 100 copies or more, being particularly preferred because these cells give a high stable level of expression of the coding sequence contained in the vector. However, cells having less than complete sections of vectors of the invention integrated into their genomes are also included within the invention if they are functionally equivalent to cells having the entire vector integrated into their genomes, in the sense that the integrated sections of the vector enable the cell to express the coding sequence and to be selected for by the use of heavy metals, as described above. Thus, cells exhibiting partial integration of vector of the invention are included in the invention if the integrated element or elements include the coding sequence operably linked to its associated promoter and the metallothionein marker sequence operably linked to its associated promoter.

The cells may be transfected by any suitable method, such as the methods disclosed by Sambrook et al (Molecular cloning: A Laboratory Manual, 1989). For example, vectors comprising nucleic acid sequences according to the invention may be packaged into infectious viral particles, such as retroviral particles. The vectors may also be introduced by electroporation, calcium phosphate precipitation or by contacting naked nucleic acid vectors with the cells in solution. Preferred methods of transfection include those described by Low et al (JBC 266; 19710–19716; 1991).

The invention also provides a process for producing proteins encoded by the coding sequence in a vector of the invention. Such processes comprise culturing cells transfected with a vector of the invention under conditions that allow expression of the coding sequence and recovering the thus produced protein. Preferred proteins that may be produced in this way include interferons, for example human interferons. β-interferons are preferred and human β-interferon is most preferred. Other proteins are interleukins (such as interleukin-12), human chorionic gonadotropin, growth factors, human growth hormone and human erythropoietin, cell membrane components, viral proteins and other proteins of biomedical relevance.

The selected cells may be cultured under any suitable conditions known in the art and these conditions may vary depending on the cell type and the type of protein being produced. The promoter for the coding sequence can be a constitutive promoter so that the protein encoded by the coding sequence is expressed in the absence of a heavy metal ion. The cells may however be cultured in the presence of a heavy metal ion, particularly in an amount which is not toxic to the cells. That can lead to higher expression of the desired protein.

The concentration of the heavy metal ion in the culture medium is typically from 100 to 200 $\mu$M. Cells may therefore be cultured in the presence of from 100 to 200 $\mu$M of a heavy metal ion selected from $Cd^{2+}$, $Cu^{2+}$ and $Zn^{2+}$, for example from 130 to 170 $\mu$M of the heavy metal ion. A useful concentration is about 150 $\mu$M, particularly when the heavy metal ion is $Zn^{2+}$. The use of $Zn^{2+}$ has a beneficial effect on the yield of β-interferon and erythropoietin production. Unexpectedly, it was observed that human β-interferon production was increased two- to three-fold and human erythropoietin production was increased three- to five-fold.

The protein that is produced may be recovered by any suitable means known in the art and the method of recovery may vary depending on the type of cells employed, the culture conditions and the type of protein being produced. Desirably, the protein produced will be purified after recovery. Substantially pure protein can thus be obtained.

The present invention enables a novel human β-interferon to be provided. This β-interferon has a high degree of sialylation. Like natural human β-interferon produced by primary diploid human fibroblasts, it is well glycosylated. However, it has a higher bioavailability than the natural β-interferon or recombinant β-interferon produced in *E. coli* (BETASERON).

The higher bioavailability of the β-interferon can be characterised. When $1.5 \times 10^6$ International Units (I.U.) of the interferon is injected subcutaneously into the back of a rabbit of about 2 kg: (a) $\geq 128$ I.U./ml of the interferon is detectable in the serum of the rabbit after 1 hour, and/or (b) $\geq 64$ I.U./ml of the interferon is detectable in the serum of the rabbit after 5 hours.

The maximum level of interferon is typically observed; after 1 hour. According to (a), therefore, 128 to 256 I.U./ml such as 140 to 190 I.U./ml of the interferon may be detectable in the rabbit serum after 1 hour. After 5 hours according to (b), $\geq 70$ I.U./ml such as $\geq 80$ I.U./ml of the interferon may be detectable in the rabbit serum. Typically according to (b), an amount of interferon in the range of 64 to 128 I.U./ml such as 80 to 110 I.U./ml can be detected.

Additionally or alternatively, the interferon can be characterised by its specific activity. It can have a specific activity in the range of from $4.8 \times 10^8$ to $6.4 \times 10^8$ I.U. per mg equivalent of bovine serum albumin protein. The specific activity may be from $5 \times 10^8$ to $6 \times 10^8$, for example from $5.2 \times 10^8$ to $5.8 \times 10^8$ such as from $5.3 \times 10^8$ to $5.5 \times 10^8$, I.U. per mg equivalent of bovine serum albumin protein.

The specific activity can be referenced to a standard, in particular the Gb23-902-531 standard distributed by the Natl. Inst. Allergy and Infectious Disease, NIH, U.S.A. Specific activity is determined according to a modification of the method of Armstrong (1971) in which 0.2 $\mu$g/ml of actinomycin D is included in the viral challenge and the viral-induced C.P.E. is read directly. The assay cells were MRC-5 fibroblasts.

The β-interferon may also be characterised by one or more of the following properties:

1. The β-interferon according to the present invention typically has an apparent molecular weight of 26,300 as determined by 15% sodium dodecyl sulphate-polyacrylamide gel electrophoresis (SDS-PAGE).

2. When injected as a neat intravenous bolus into a rabbit, the half life of the interferon is typically in the range of from 12 to 15 min such as about 13½ min. The bolus is injected into the rabbit ear vein and blood samples are withdrawn from the rabbit ear artery. Rabbit serum is assayed for the antiviral activity of the interferon according to the modification of the method of Armstrong (1971).

3. The antiviral activity of the interferon in a human hepatoblastoma cell line (HepG2) is at least equal to and, typically, about 1.5 times the activity of natural β-interferon from primary diploid human fibroblast cells. The interferon is also about 2.2 times more effective than betaseron in protecting Hep2 cells against a viral challenge. Antiviral activity is again determined according to the modified method of Armstrong (1971). Actinomycin D was omitted in the antiviral determination in HepG2 cells. The oligosaccharides associated with the β-interferon of the invention may also characterise the β-interferon. The β-interferon carries oligosaccharides which can be characterised by one or more of the following features:

1. Neutral (no acidic substituents): 5 to 15%, preferably about 10%. Acidic: 95 to 85%, preferably about 90%

2. The total desialylated oligosaccharide pool is heterogeneous with at least six distinct structural components present in the pool.

3. Matrix-Assisted Laser Desorption Ionisation—Time of Flight (MALDI-TOF) mass spectrometry and high resolution gel permeation chromatography data are summarised as follows:

| Mass detected | Composition | Calculated Mass | gu equivalent |
|---|---|---|---|
| 1786.2 | 5Hex, 4HexNAc, 1 2AB, Na | 1782 | 11.1 |
| 1929.9 | 5Hex, 1dHex, 4HexNAc, 1 2AB, Na | 1928 | 12.2 |
| 2295.5 | 6Hex, 1dHex, 5HexNAc 1 2AB, Na | 2293 | 14.5 |
| 2660.1 | 7Hex, 1dHex, 6HexNAc 1 2AB, Na | 2658 | 17.6 |
| 3019.1 | 8Hex, 1dHex, 7HexNAc, 1 2AB, Na | 3023 | 20.7 |

The carbohydrate moiety of the β-interferon of the invention consists of bi-, tri- and tetra-antennary complex type N-linked oligosaccharides. These oligosaccharides contain repeating lactosamine(s). About 30 to 80%, for example 35 to 60% or 35 to 50%, of the oligosaccharides are bi-antennary oligosaccharides. About 15 to 65%, for example from 25 to 50% or 25 to 40%, of the oligosaccharides are tri-antennary oligosaccharides. About 5 to 55%, for example from IS to 45% or 20 to 40%, of the oligosaccharides are tetra-antennary oligosaccharides.

The β-interferon of the invention exhibits antiviral activity, cell growth regulatory activity and an ability to regulate the production of intracellular enzymes and other cell-produced substance. Accordingly, the β-interferon may be used to treat various viral and oncologic diseases such as hepatitis B, hepatitis C, viral encephalitis, viral pneumonia, viral warts, AIDS/nasopharyngeal carcinoma, lung cancer, melanomas,CML renal cell carcinoma and brain tumours as well as diseases like multiple sclerosis, hemangiomas and cervical intraepithelial neoplasia.

Pharmaceutical compositions that contain the β-interferon of the invention as an active principal will normally be formulated with an appropriate pharmaceutically acceptable carrier or diluent depending upon the particular mode of administration being used. For instance, parenteral formulations are usually injectable fluids that use pharmaceutically and physiologically acceptable fluids such as physiological saline, balanced salt solutions, or the like as a vehicle. Oral formulations, on the other hand, may be solids, e.g. tablets or capsules, or liquid solutions or suspensions. The interferon of the invention will usually be formulated as a unit dosage form that contains from $10^4$ to $10^9$, more usually $10^6$ to $10^7$, I.U. per dose.

The interferon may be administered to humans in various manners such as orally, intravenously, intramuscularly, intraperitoneally, intranasally, intradermally, and subcutaneously. The particular mode of administration and dosage regimen will be selected by the attending physician taking into account the particulars of the patient, the disease and the disease state involved. For instance, viral infections are usually treated by daily or twice daily doses over a few days to a few weeks; whereas tumor or cancer treatment involves daily or multidaily doses over months or years.

The interferon may be combined with other treatments and may be combined with or used in association with other chemotherapeutic or chemopreventive agents for providing therapy against viral infections, neoplasms, or other conditions against which it is effective. For instance, in the case of herpes virus keratitis treatment, therapy with interferon has been supplemented by thermocautery, debridement and trifluorothymidine therapy.

The following Examples illustrate the invention.

BRIEF DESCRIPTION OF THE DRAWINGS

FIG. 1 shows the results of immunoblot analysis carried out on CHO cells transfected with DPPIV sequences under the control of various promoters;

FIGS. 2 to 4 are vector maps of plasmids pMMTN, pMMTC and pBPV respectively. The multiple cloning site (MCS) is SEQ ID NO:7.

FIG. 5(b) shows the results of a Western Blot of purified GS38-IFNβ. Purified IFNβ produced by primary human diploid fibroblasts (lanes 1 and 2) and GS38-IFNβ (lanes 3 and 4) were subjected to SDS-PAGE (15%). The proteins were then blotted onto nitrocellulose membrane and probed with an anti-IFNβ monoclonal antibody (Accurate Chem, New York.) The amounts of IFNβ activity in the various lanes are $0.1 \times 10^6$, $0.05 \times 10^6$, $0.14 \times 10^6$ and $0.56 \times 10^6$ I.U. in lanes 1, 2, 3 and 4. The molecular weights in kda are indicated in the figure.

FIG. 13 concerns expression of human erythropoietin from wild type CHO cells transfected by the new vector containing the EPO instead of the IFNβ gene. Cells of the indicated clones (lane 1 to 14) were seeded onto 35 mm (in diameter) culture dishes. Upon confluency, 1 ml of culture medium was added to each of them and cultured for 24 hrs. The media were harvested and 10 µl of each, together with a control 50 ng of human erythropoietin (lane 15) were resolved by SDS-PAGE and analyzed by Western blot using the Amersham ECL detection system.

EXAMPLE 1

Figure 5A:
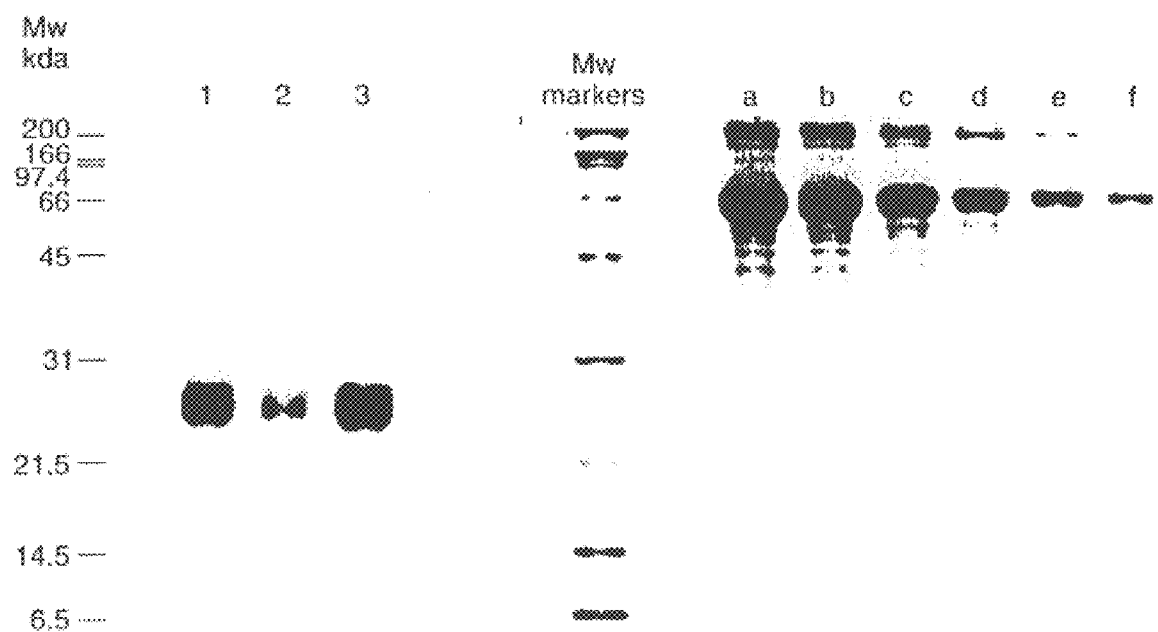
FIG. 5(a) shows the results of SDS-PAGE (15%) analysis of purified GS38-IFNβ. The molecular weight markers are from BioRad (California). The molecular weight of the markers are indicated in kda. The amount of GS38-IFNβ in lane 1, 2 and 3 are $0.8 \times 10^6$ I.U., $0.2 \times 10^6$ I.U. and $1.1 \times 10^6$ I.U. respectively. The amount of bovine serum albumin in lanes a, b, c, d, e and f are 5 μg, 3.5 μg, 2.5 μg, 1.5 μg, 0.5 μg, 0.25 μg.

Identification of MSV-mMT1 as a powerful promoter for wild-type CHO cells

The strengths of 5 promoter/enhancer systems were compared. These were:

- mouse metallothionein gene 1 promoter flanked upstream with mouse sarcoma virus enhancer (MSV-mMT1: mMT1 is described by Glanville et al (1981) Nature 292, 267–269; MSV is described by Dhar et al (1980) PNAS 77, 3937–3941);
- the cytomegalovirus early promoter (CMV);
- RSV-SV40 (a fusion between the rous sarcoma virus [RSV] enhancer and SV40 early promoter);
- RSV-mouse mammary tumour virus long terminal enhancer/promoter (RSV-MMTV); and
- SR-α promoter (Yutaka Takebe et al (1988) Mol. Cell. Biol. 8, 466–472).

For this comparison, an EcoRI-XhoI cDNA encoding full-length dipeptidyl peptidase IV (DPPIV) (Hong and Doyle (1988) J. Biol. Chem. 263, 16892–16898) was cloned into the respective expression vectors so that DPPIV expression was under the control of MSV-mMT1, CMV, RSV-SV40, RSV-MMTV, or SR-α, respectively.

For MSV-mMT1, the DPPIV fragment was inserted into XhoI-NotI sites of pMMTN vector (FIG. 2); for CMV, the fragment was inserted into the EcoRI and XhoI sites of pXJ41neo vector (Zheng and Pallen (1992); Nature, 359, 336–339); for RSV-SV40, see Low et al (1991) J. Biol. Chem. 266, 19710–19716); for RSV-MATV, the fragment was inserted into the NhoI-XhoI sites of pMAMneo vector (from Clontech: catalogue number 6104-1; described by Lee et al (1981): Nature 294, 228 and by Sardet et al (1989): J. cell 56, 271); for SR-α, the fragment was inserted into the XhoI-BamHI sites of pSRalpha/neo vector (Yutaka Takebe et al (1988) MCB 8, 466–472; Nilsson et al, J. Cell Biol. 120, 5–13, 1993).

Each expression vector was transfected into CHO cells and stably transfected cells were pooled for each vector. The strength of each expression vector was then measured by the protein levels of DPPIV using immunoblot analysis, with the amount of DPPIV detected giving an indication of the strength of each expression system.

Immunoblot analysis to detect DPPIV in these transfected cells was performed as described by Hong et al (1989) (Biochemistry 28, 8474–8479). Briefly, cells were washed with Tris-buffered saline (TBS) (20 mM Tris, pH7.2, 150 mM NaCl), and then extracted with 1% TRITON X-100 in TBS with 1 mM PMSF. The extracts were cleared of cell debris by centrifugation. The protein concentration of the extracts was determined using a BSA kit (Pierce Chemical Co.).

About 100 µg of proteins extracted from respective transfected cells were resolved by SDS-PAGE and then analysed by immunoblot as previously (Hong et al (1989) Biochemistry 28, 8474–8479). The results shown in FIG. 1 show that the MSV-mMT1 expression system (lane 2) is much stronger than the remaining widely used ones.

EXAMPLE 2

Description of plasmid pMMTC

Based on the above, a powerful expression vector pMMTC was constructed using MSV-mMT1 to drive the expression of foreign genes in conjunction with two selection markers (the neo gene for transfected cells and the human metallothionein gene IIA for cells that have integrated multiple copies of the vector into their genomes).

pMMTC (FIG. 3) is a mammalian cell expression vector. The gene to be expressed is cloned into XhoI and/or NotI sites so that the expression of the gene is driven by a control region (MSV-mMT1) that comprises the mouse sarcoma virus enhancer (MSV) and the mouse metallothionein gene 1 promoter. The SV40 splicing region and the polyadenylation site serve to terminate the transcription and to ensure proper control of post-transcriptional events.

The bacterial neo gene is flanked upstream with the SV40 origin of replication and the SV40 early promoter and downstream by the SV40 splicing region and the polyadenylation site. This neo expression unit confers transfected mammalian cells resistance to geneticin (G418) and also confers upon transformed *E. coli.* resistance to kanamycin.

The pBR322 origin of replication (Ori) serves as the origin for autonomous replication of the plasmid DNA in *E. coli*. The human metallothionein structural gene IIA, which confers resistance to heavy metal ions such as $Cd^{2+}$ on mammalian cells, was used to select for mammalian transfectants that have integrated multiple copies of the plasmid. Construction of mammalian expression vector pMMTC Plasmid pRSN (Low et al., JBC 266;19710–19716, 1991) was cut with the restriction enzyme BamHI and resolved by agarose gel electrophoresis. A DNA fragment of about 2685 bp was gel-purified. This BamHI fragment contains the expression unit for the *E. coli* neo gene in both mammalian cells and *E. coli*.

Plasmid pBPV (Pharmacia: product number 27-4390; see FIG. 4 and below for full description) was cut with restriction enzyme BamHI and then treated with calf intestinal alkaline phosphatase (CIAP). After being resolved by agarose gel electrophoresis, a BamHI fragment of about 4570 bp was gel purified. This 4570 bp fragment contains the pBR322 origin of replication in *E. coli,* the Ampicillin (Amp) resistance gene and an expression cassette composed of the mouse sarcoma virus enhancer and the mouse metallothionein gene 1 promoter followed by a multiple cloning site and the SV40 splicing junction and polyadenylation signal.

This 4570 bp fragment was ligated to the above 2685 bp BamHI fragment. The resulting plasmid was named pMMTN (FIG. 2). A plasmid phMT (Karin et al (1982): Nature 299, 797–802) was cut with HindIII and blunt-ended with Klenow fragment of DNA polymerase I. A 3100 bp fragment, containing the human metallothionein gene II A, was gel-purified. Plasmid pMMTN was cut with ScaI (which is within the Ampicillin resistance gene), treated with CIAP, and then ligated with the 3100 bp fragment obtained from phMT.

The product of this ligation was transformed into *E. coli.* Selection was performed for kanamycin resistance (conferred by the neo gene) and Amp sensitivity (due to the insertion of the 3100 bp fragment into the structural gene for Amp resistance). The final plasmid construct was confirmed by restriction enzyme digestion and was named pMMTC. pMMTC is about 10350 bp in length.

GENEOLOGY: pBPV (12516 bp)

(Nucleotide numbers refer to numbering in the reference)
MSV enhancer (388 bp)

Dhar. R. et al, Proc, Natl. Acad Sci. U.S.A. 77, 3937 (1980). Nuc 529-142

BamHI/BglII linker CCGGATCTG

5'-end of metallothionein promoter (295 bp) Nuc 1-295

3'-end of metallothionein promoter (368 bp) Glanville, N. et al Nature 292 267 (1981). Nuc 300-68

Multiple cloning site and additional nucleotides from construction CTCGAGCCGCGGCCGCTTCGAGG (SEQ ID NO:1)

SV40 small T-antigen splice (612 Patent Bulletin No.) and polyadenylation (235 Patent Bulletin No.) signals Buchman, A. R. et al DNA Tumor Viruses, Cold Spring Harbor Laboratory, pg 799 (1980), Nuc 4713-4102 and 2772-2538

BPV genome (7945 bp)

Chen E. Y. et al Nature 299,529 (1982). Nuc 4451-7945 and 1-4450 pML2: a derivative of pBR322 with a deletion between bases 1,095 and 2,485 (2,632) bp)

(1) Balbas. P., et al Gene 50.3 (1986).

(2) Sarvor. N. et al Proc. Natl Acad. Sci U.S.A. 79,7147 (1982). Nuc 376-1095, 2485-4363 and 1-33

BglII/BamHI linker GAGATCCGG

EXAMPLE 3
Insertion of human β-interferon expression DNA into pMMTC

The β-interferon coding sequence was retrieved from human genomic DNA by PCR with two oligonucleotides. The 5' oligo (GGGGTACCATGACCAACAAGTGTCTCCTC, SEQ ID NO:2) was modified in such a way that the sequence (CCACCATG) around the initiation ATG codon favours efficient translational initiation (Kozak (1984): NAR 12,857–872). The sequence of the 3' oligo was GGAAT-TCTTCAGTTTCGGAGGTAACCTGT (SEQ ID NO:3). This modified expression sequence for β-interferon was inserted into the XhoI and NotI sites of pMMTC. The insertion and correct orientation was confirmed by restriction mapping, PCR or sequencing. The resulting plasmid was named pMMTC/IFNβ.

EXAMPLE 4
Establishment of CHO cell clones that constitutively secrete high levels of functional human β-interferon CHO cells were transfected with pMMTC/IFNβ as described (Low et al., J. Biol. Chem. 266;19710–19716, 1991). Cells were selected in G418 (800 µg/ml) for 7–10 days to allow growth of stably transfected cells. The cells were then incubated in medium with 50–100 µM $Zn^{2-}$ ions for 24 to 48 hr to induce the expression of human metallothionein and then incubated in a medium with step-wise increasing concentration of $Cd^{2+}$ (final concentration 200 µM). Individual colonies was cloned and expanded. The culture medium from the cloned cells accumulated β-interferon to a concentration of $10^6$ I.U./ml or more and $10^6$ I.U. or more of β-interferon was secreted by $10^6$ cells in at most 24 hr.

EXAMPLE 5
Production of human β-interferon in CHO cells

Wild type Chinese hamster ovary cells CHO-K1 line (ATCC CCL-61) were propagated in Dulbecco's Minimum Essential Medium (DMEM) containing 10% fetal calf serum. Cells were grown at 37° C. in an atmosphere of 5% carbon dioxide. These cells were transfected with the pMMTC/IFNβ plasmid to secrete constitutively high levels of functional human β-interferon. Cells were selected as described in Example 4.

During the selection with $Cd^{2-}$, clones of transfected cells were measured for the antiviral activity of β-interferon to show that they were constitutively secreting high levels of functional human β-interferon. Antiviral activity was measured according to the method of Armstrong (Armstrong, Applied Microbiology 21, 723, 1971) modified by including 0.2 µg ml of actinomycin D in the viral challenge and reacting the viral-induced C.P.E. directly. From these measurements, individual colonies were isolated and expanded. Indeed several lines were found to produce $10^6$ I.U./ml to $10^7$ I.U./ml of β-interferon when grown in plastic roller bottles.

One of these cell lines, GS38, was maintained in culture over 12 months to test its ability to maintain a consistent high level of β-interferon production. The GS38 cell line was maintained in plastic culture flasks (80 $cm^2$) in DMEM containing lot fetal calf serum, 100 µg/ml penicillin, 100 µg/ml streptomycin, 2.5 µg/ml amphotericin and 150 µM zinc sulphate ("regular medium"). The seeding of a roller bottle (1700 $cm^2$) was done by adding a culture flask (80 $cm^2$) of GS38 cells into one 1700 $cm^2$ roller bottle and the cells were maintained in 200 ml of regular medium.

The medium from the roller bottle was discarded on day 2 and day 4 and replenished with 200 ml of fresh regular medium each time. On day 6, the regular medium was discarded and the roller bottle was replenished with 300 ml of serum-free DMEM medium which contained 2.5 mg/ml of human serum albumin containing the list of additional ingredients listed in Table 1 ("serum-free medium").

TABLE 1

| Component | Conc. | |
| --- | --- | --- |
| Penicillin | 100 | µg/ml |
| Streptomycin | 100 | µg/ml |
| Amphotericin B | 2.5 | µg/ml |
| $ZnSO_4$ | 150 | µM |
| EX-CYTE (trade mark)* | 1:1000 | |
| Transferrin | 2.5–5.0 | µg/ml |
| Insulin | 5 | µg/ml |

*EX-CYTE is an aqueous liquid supplement from human serum sold by Bayer, Illinois, U.S.A..

On day 7, the serum-free medium was discarded and replenished with another 300 ml of serum-free medium. On day 8, the serum-free medium was again discarded and replenished with another 300 ml of serum-free medium. On day 9, the serum-free medium (300 ml) was harvested and replenished by another 300 ml of serum-free medium. This harvesting procedure was repeated daily for another 14 days.

From each roller bottle, a total of about 4.2 liters of GS38-produced β-interferon (or GS38-IFNβ) was harvested. From $2.4 \times 10^6$ to $3.6 \times 10^6$ I.U. of β-interferon was obtained per ml of crude harvest from GS38 cells. This is equivalent to 1.35 mg to 2 mg of GS38-IFNβ per day from one roller bottle of GS38 cells from about 5 mg to 6.7 mg per liter of GS38-IFNβ from 1 liter of crude harvest per day. The crude GS38-IFNβ, when purified to homogeneity, had a specific activity of $5.37 \times 10^8$ I.U./mg of protein (bovine serum albumin), standardized to the Gb23-902-531 standard (an NIH reference standard distributed by the Natl. Inst. Allergy and Infectious Diseases, NIH, U.S.A.).

The harvest of crude GS38-IFNβ was pooled and subjected to purification by a combination of affinity and ion exchange column chromatography purification (Tan et al, J. Biol. Chem. 254, 8067–8073, 1979; Edy et al, J. Biol. Chem.

252, 5934–5935, 1977; Knight et al PNAS U.S.A. 73, 520–523, 1976). Pure GS38-IFNβ was obtained with about 70–80% recovery. The pure GS38-IFNβ when analysed was found to be homogeneous according to the following criteria of homogeneity:

A single molecular mass of an apparent molecular weight of 26,300 was observed on SDS-PAGE (15%) (FIG. 5a). This is similar to the molecular weight of a natural β-interferon produced by primary human diploid foreskin fibroblasts after the superinduction procedure of Tan et al (1970 and 1973) (see FIG. 5b). Note that the broad range molecular weight markers obtained from BIO-RAD were slightly different from the ones used as previously reported by ourselves and others. The identity of these g-interferons (GS38-IFNβ and human fibroblast-produced β-interferon) were verified by Western Blot (FIG. 5b) to belong to a single average molecular mass of 26,300.

When subjected to hplc (Hewlett Packard 1090) C18 column chromatography, the protein peak of the material corresponded directly with the antiviral activity of interferon.

When subjected to amino acid sequencing, the material had the sequence of β-interferon.

The amount of GS38-IFNβ produced by GS38 cells over 12 months was found not to change much. The cells produced from 2.35 to $3.6 \times 10^6$ I.U./ml of GS38-IFNβ throughout that period.

Five biological activities of GS38-IFNβ were assayed. The β-interferon from primary human fibroblasts referred to below was produced from early to mid-passage primary human foreskin fibroblasts according to the superinduction method of Tan et al (1970) with additional priming of cells by 100 I.U. of β-interferon about 16 hours before superinduction. The resulting β-interferon was purified by affinity chromatography. The five activities which were assayed are:

1. Antiviral activity of β-interferon was assayed on either human MRC5 fibroblasts or human hepatoblastoma cell line (HepG2) after the modified method of Armstrong (1971). Accordingly, the specific activity of GS38-IFNβ was $5.37 \times 10^8$ I.U./mg protein as assayed in MRC5 human fibroblasts and referenced to the NIH β-interferon standard. The antiviral activity of GS38-IFNβ in HepG2 cells was at least equal to or 1.5 times more effective than natural β-interferon from human fibroblast cells. GS38-IFNβ is also about 2.2 times more effective than BETASERON (recombinant human β-interferon produced in E. coli) in protecting HepG2 cells against a viral VSV challenge.

2. Cell growth inhibition assay of β-interferon (Tan, Nature 260, 141–143, 1976) on the human hepatoblastoma cells as described for primary human cells but applied to HepG2 cells was performed. However, the assay was performed in 2 cm² wells containing 1 ml of regular medium and an initial HepG2 cell count of 3 to $5 \times 10^4$ cells/well. Accordingly, GS38-IFNβ was as effective as natural primary human diploid fibroblast β-interferon in inhibiting HepG2 cell growth as measured by this in vitro assay.

3. Pharmacokinetics of subcutaneously injected β-interferon was performed in rabbits. Purified β-interferon from either GS38 or primary human fibroblasts, or BETASERON from E. coli, was separately reconstituted in 4 mg of human serum albumin in 1 ml of phosphate buffered saline (0.15M NaCl) pH 7.0 containing 20 mg trehalose. $0.7 \times 10^6$ or $1.5 \times 10^6$ I.U. of an interferon was separately injected subcutaneously into the back of albino rabbits of a weight of about 1.5 kg and about 2 kg respectively.

Figure 10A:
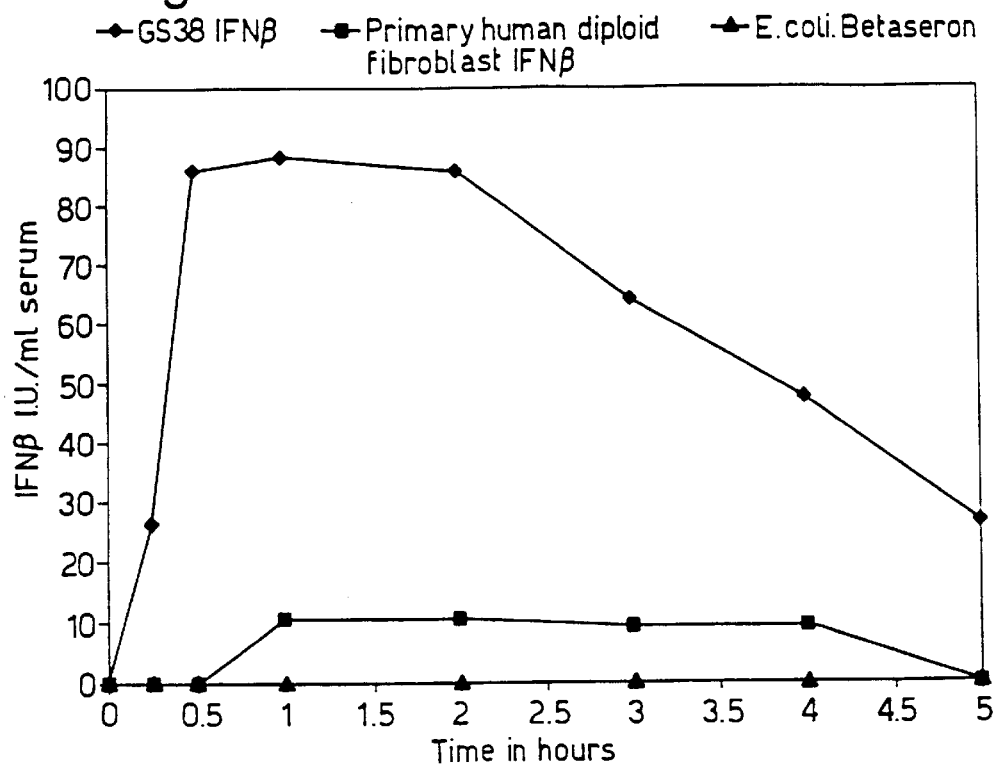
FIG. 10(a) shows the serum levels of IFNβ in rabbits after subcutaneous injection with $0.7 \times 10^6$ I.U. of IFNβ produced by GS38 cells (♦), primary human diploid fibroblasts (■) or E. coli [BETASERON (▲)]. The weight of rabbits injected was about 1.5 kg.
Figure 10B:
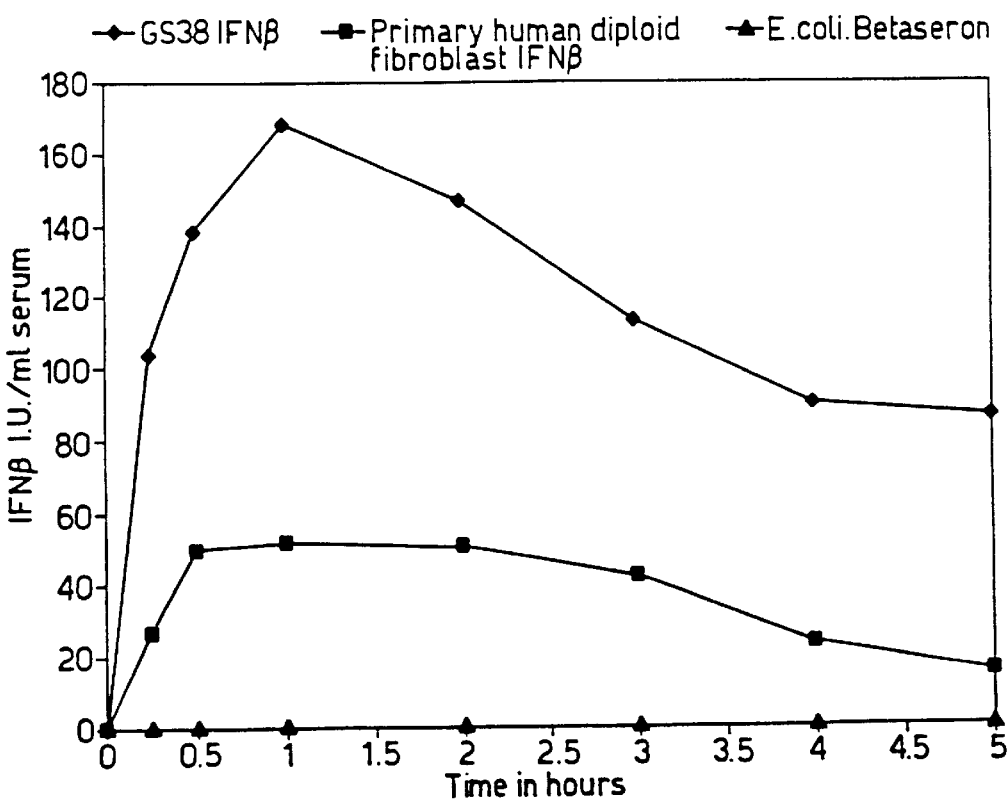
FIG. 10(b) shows the serum levels of IFNβ in rabbits after subcutaneous injection with $1.5 \times 10^6$ I.U. of IFNβ produced by GS38 cells (♦), primary human diploid fibroblasts (■) or E. coli [BETASERON (▲)]. The weight of rabbits injected was about 2.0 kg.

Whole blood (500 μl) was withdrawn from the rabbits at 15 min., 30 min., 1 h, 2 h, 3 h, 4 h and 5 h. Serum from the drawn blood was then assayed for the antiviral activity of β-interferon according to the modified method of Armstrong (1971). The results are presented in FIGS. 10 (a) and (b) showing that GS38-IFNβ has a higher bio-availability than β-interferon produced from primary human fibroblasts and BETASERON.

The maximum level of GS38-IFNβ (128–256 I.U./ml) occurred after 1 hour, and significant levels of GS38-IFNβ (64–128 I.U./ml) were found for at least 5 hours in the serum of rabbits injected with $1.5 \times 10^6$ I.U. of GS38-IFNβ. This was unexpected. It is generally known that subcutaneous or intramuscular injection of human β-interferon results in no or low serum levels of circulating human β-interferon.

Figure 11:
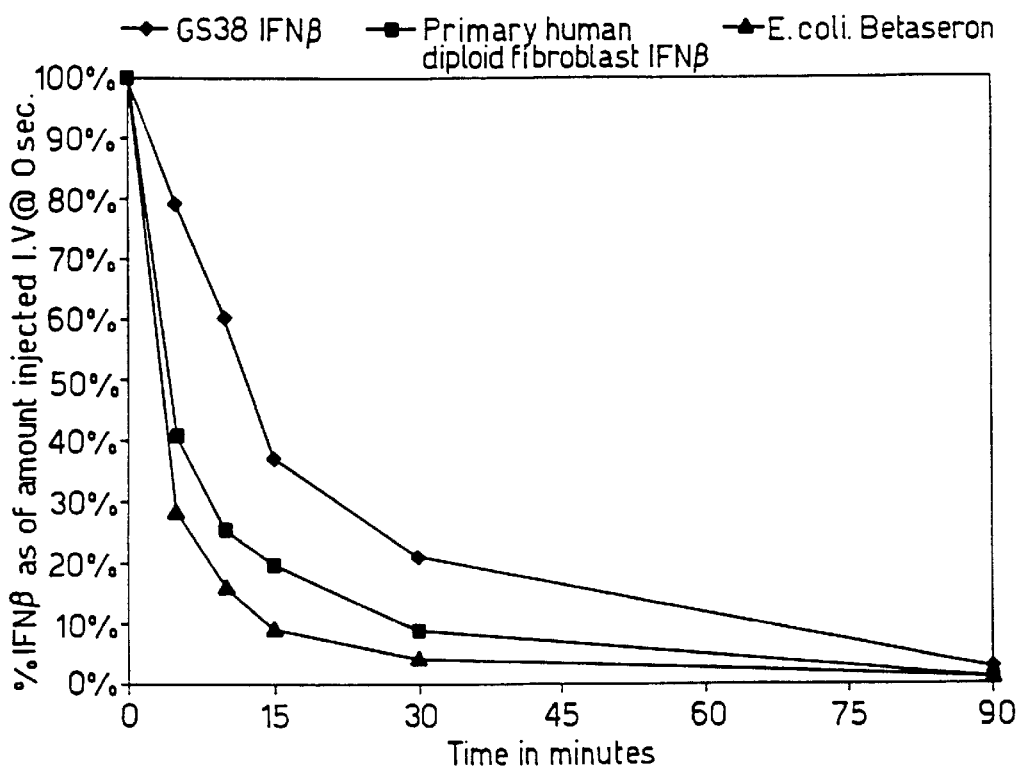
FIG. 11 shows the decay of serum IFNβ levels in rabbits (about 2 kg) injected intravenously with $0.7 \times 10^6$ I.U. of three different kinds of IFNβ prepared from GS38 cells (♦), primary human diploid fibroblasts (■) or E. coli [BETASERON (▲)].

4. Pharmacokinetics of a neat intravenous bolus of β-interferon in rabbits was also performed. 1 ml of each kind of β-interferon (GS38-IFNβ, natural interferon produced from primary human fibroblasts and E. coli BETASERON) containing approximately equal amounts of β-interferon ($0.7 \times 10^6$ I.U.) was injected into the rabbit ear vein. Blood (500 μl) was withdrawn at 5 min, 10 min, 15 min, 30 min, and 90 min. The serum was assayed for the antiviral activity of β-interferon according to the modified method of Armstrong (1971). The result is shown in FIG. 11 where the half-life (t½) of GS38-IFNβ is 13.6 min, compared to primary human fibroblast-produced β-interferon (t½= 4.4 min) or BETASERON (t½=3.8). According to standard methodology, the total amount of β-interferon injected was divided by the blood volume to estimate the starting concentration of β-interferon at time zero. The blood volume was assumed to be 5% of the body weight of the rabbit. The time to decay to 50% of this starting concentration was t½.

Figure 12:
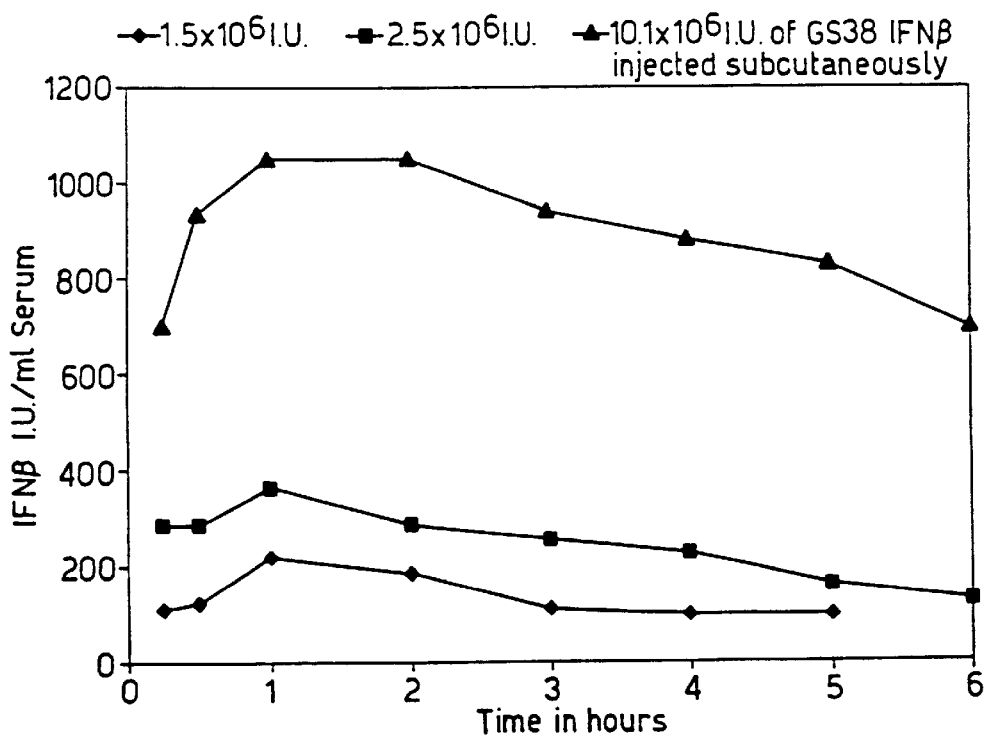
FIG. 12 shows the dosage effect of subcutaneously injected GS38-IFNβ on serum levels of circulating GS38/IFNβ. Levels of serum GS38-produced IFNβ levels in rabbits (2 kg) injected subcutaneously with [$1.2 \times 10^6$ I.U., (♦), $2.5 \times 10^6$ I.U. (■) and $10.1 \times 10^6$ I.U. (▲) of GS38 IFNβ.

5. The dosage effect of injecting increasing amounts of GS38-IFNβ was investigated. Rabbits of about 2 kg were injected subcutaneously with increasing amounts of GS38-IFNβ, in particular with $1.2 \times 10^6$ I.U., $2.5 \times 10^6$ I.U. and $10.1 \times 10^6$ I.U. of GS38-IFNβ. The results in FIG. 12 show that increasing doses of GS38-IFNβ injected subcutaneously proportionally increase the measurable level of GS38-IFNβ in the serum of the injected rabbits.

EXAMPLE 6

Analysis of oligosaccharides associated with GS38-IFNβ

GS38-IFNβ is a glycoprotein. The oligosaccharides associated with GS38-IFNβ were quantitatively released and recovered. The N and O linked glycans were released by treatment with anhydrous hydrazine. In this procedure, the protein backbone is converted into amino acid hydrazones. Intact reducing glycans are separated, recovered and labelled fluorimetrically with 2-aminobenzamide.

More specifically, a sample of GS38-IFNβ (1–2 mg) was subjected to vigorous sample preparation, involving lyophilisation (<50 mill Torr, >24 hours), introduced to a GLYCO PREP 1000 (an automated system for release and recovery of glycans from glycoproteins, (Oxford Glyco Systems, GB) and the oligosaccharides were released and recovered using the "N+O" program. The sample was fluorescently labelled by reductive amination with 2-aminobenzamide.

The sample was then applied to Whatman 3MM chromatography paper and subjected to ascending paper chromatography using 1-butanol/ethanol/water (4:1:1). The labelled sample remaining at the origin was subsequently eluted with water. This procedure leads to the quantitative (and non-selective) recovery of the total pool of oligosaccharides associated with the GS38-IFNβ sample as 2-aminobenzamide labelled oligosaccharide.

The pool of labelled oligosaccharides was fractionated and analysed as follows:

The labelled oligosaccharides were analysed for their charge distribution by hplc anion exchange chromatography. Accordingly, an aliquot of the total pool of 2-aminobenzamide-labelled oligosaccharides was subjected to hplc anion exchange chromatography on a GLYCO SEP C column (Oxford GlycoSystems, GB) using acetonitrile and ammonium acetate as eluent. The labelled glycans eluted from the column were detected using the fluorometer at λex=356 mm λem=450mm. The resultant chromatogram is shown in FIG. 6.

Figure 7:
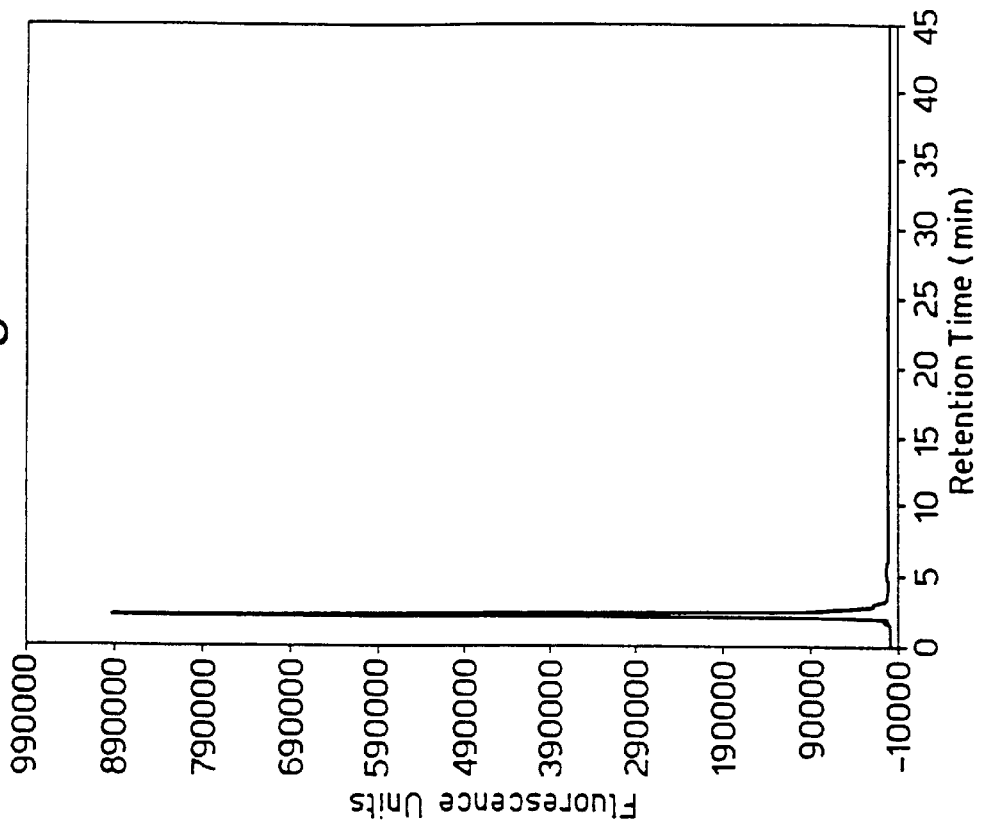
FIG. 7 is a hplc anion exchange chromatogram of the oligosaccharides associated with GS38-IFNβ after neurammidase treatment.
Figure 6:
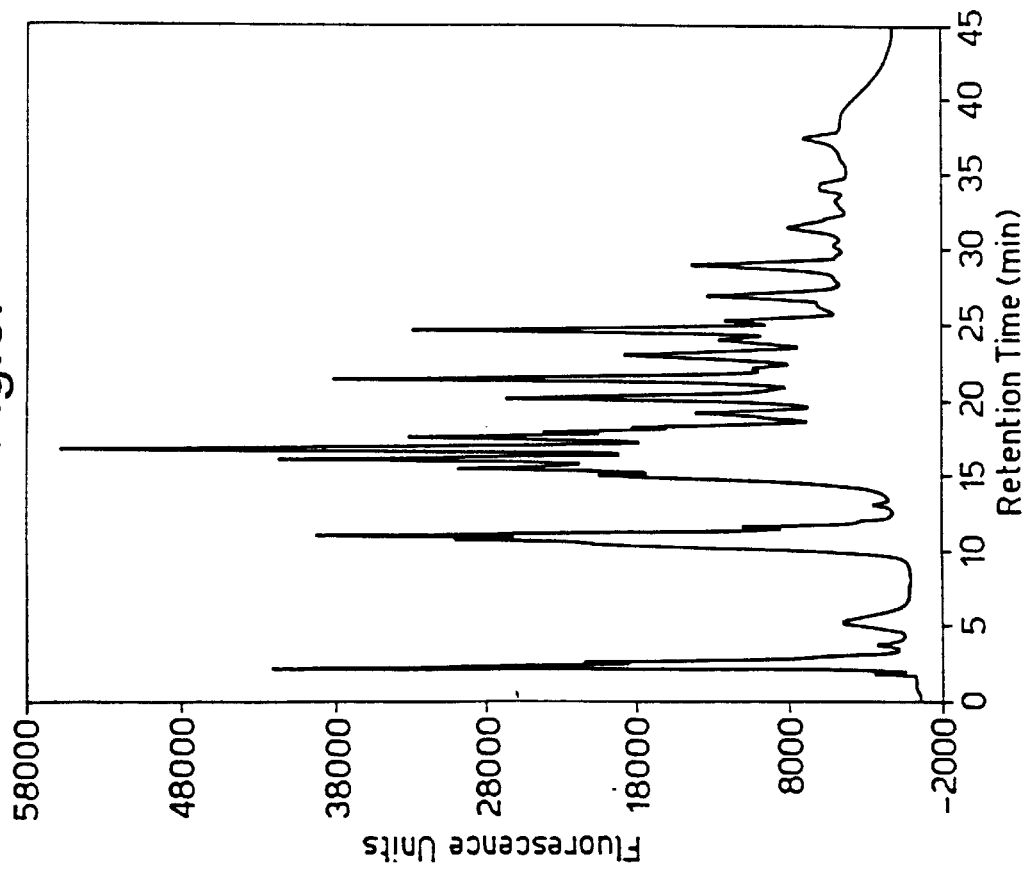
FIG. 6 is an hplc anion exchange chromatogram of the oligosaccharides associated with GS38-IFNβ.

It is shown from FIG. 6 that the oligosaccharides associated with GS38-IFNβ consist of both neutral and acidic components. To determine the nature of the acidic substituents, an aliquot of the total pool of fluorescently labelled oligosaccharides was incubated with neuraminidase (derived from *Arthrobacter ureafaciens*). An aliquot was again subjected to GLYCO SEP C chromatography. The resultant chromatogram is shown in FIG. 7.

No acidic oligosaccharides were detectable after incubation with the neuraminidase. Hence, the oligosaccharides that carry an acidic substituent do so only because they possess a covalently linked non-reducing terminal outer-arm sialic acid residue. The relative molar content of neutral and acidic oligosaccharides in the total pool was determined by integration of the chromatographic peaks (FIG. 6). The results are as follows:

| Neutral | 10% ± 0.8% (to 1 s.d.) |
|---|---|
| Acidic | 90% ± 0.6% (to 1 s.d.) | s.d. = standard deviation

2. Size-distribution of the total pool of deacidified oligosaccharides released from GS38-IFNβ

Figure 8:
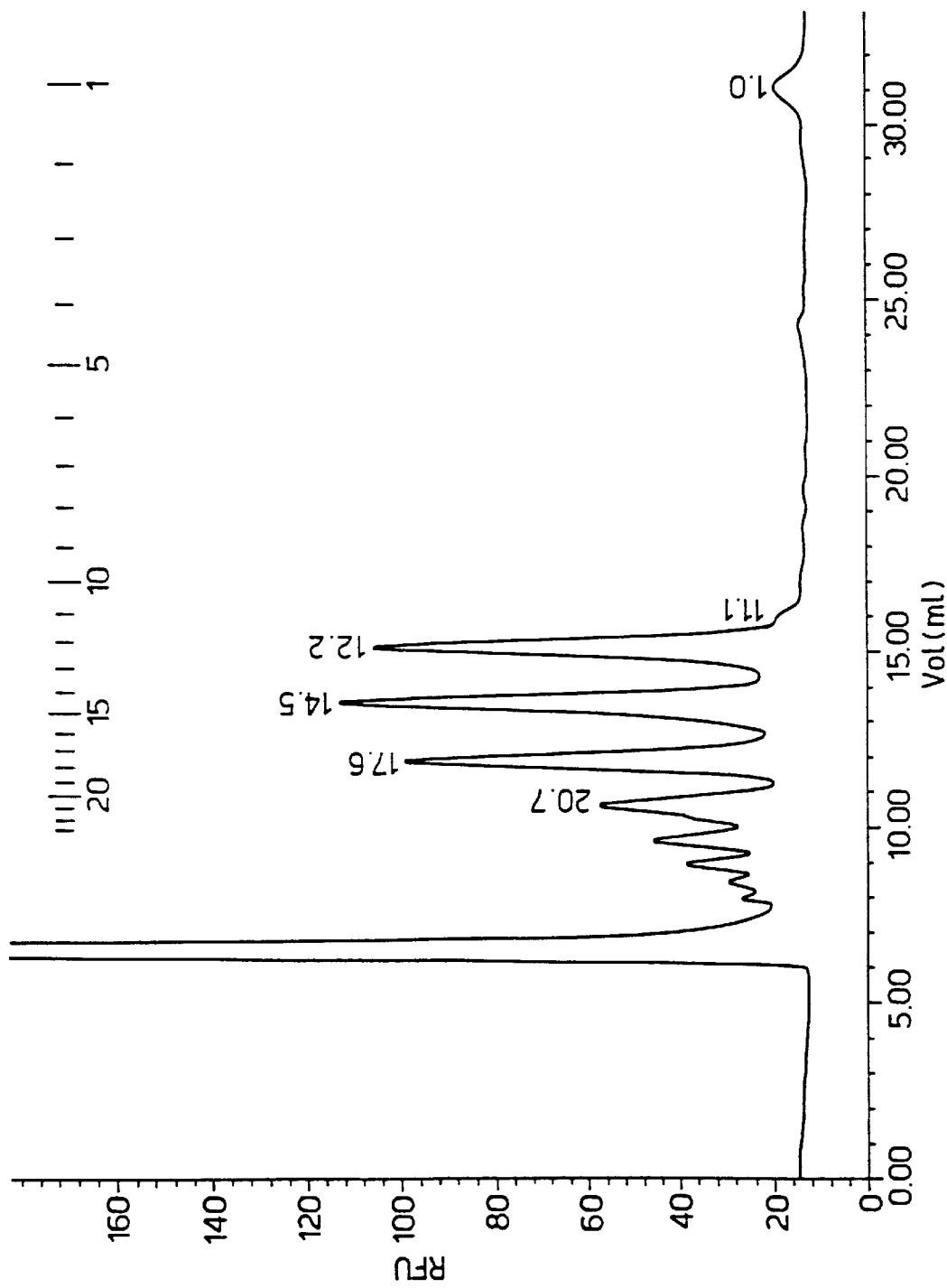
FIG. 8 is a high resolution gel permeation chromatogram of the oligosaccharides associated with GS38-IFNβ.

An aliquot of the total pool of deacidified 2-aminobenzamide labelled oligosaccharides was subjected to high resolution gel permeation chromatography using the RAAM 2000 (Oxford Glyco Systems, GB). The resulting gel permeation chromatogram is shown in FIG. 8. As a note of explanation, the fluorescently labelled deacidified oligosaccharides were suspended in an aqueous solution of a partial acid hydrolysate of dextran, and applied to a RAAM 2000 (eluent of water, maintained at 55° C., constant flow 80 μl/min over 10.6 hours). Detection was by an in-line fluorescence flow detector (to detect fluorescently labelled sample), and an in-line differential refractometer (to detect individual glucose oligomers).

Numerical superscripts in FIG. 8 represent the elution position, of the non-fluorescent, co-applied, glucose oligomers in glucose units (gu), as detected simultaneously by refractive index. The hydrodynamic volume of individual 2-amino-benzamide labelled oligosaccharides is measured in terms of glucose units, as calculated by cubic spline interpolation between the two glucose oligomers immediately adjacent to the fluorescently labelled oligosaccharide.

It is clear that at least 6 discrete oligosaccharide are identifiable within the dextran calibration range, and their effective hydrodynamic volumes are as follows:

| 20.7 gu | 14.5% |
|---|---|
| 17.6 gu | 23.4% |
| 14.5 gu | 29.8% |
| 12.2 gu | 26.4% |
| 11.1 gu | 2.1% |
| 1.0 gu | 3.8% |

Annotation of hydrodynamic volume is accurate to ±0.1 gu for all volumes ≦20 gu. The conjugation of the glycans with 2-aminobenzamide (2-AB) decreases the hydrodynamic volume of the glycans by a constant value. The hydrodynamic volume of the 2-AB labelled glycans (λf) is calculated from hydrodynamic volume of the unreduced glycans (λ) using the following equation:

$$\lambda f = 1.2\lambda - 1.96$$

3. Molecular weight distribution of the de-acidified glycans released from GS38-IFNβ

Figure 9:
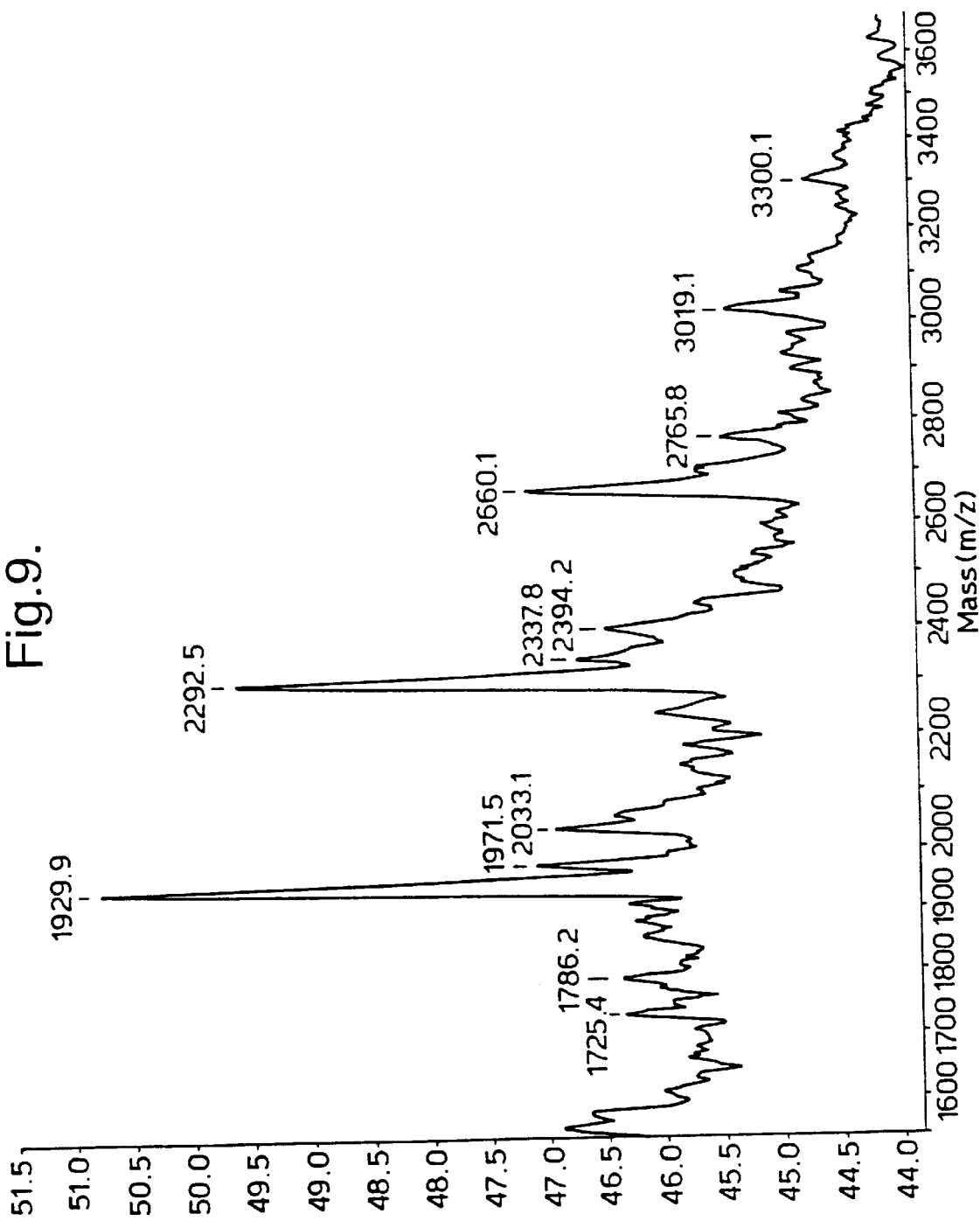
FIG. 9 shows the molecular weight distribution of the de-acidified glycans released from GS38-IFNβ by MALDI-TOF mass spectrometry.

Since peaks were detected outside the dextran calibration range (FIG. 8) and particularly in the void volume, it was necessary to obtain a molecular weight distribution in order to establish what carbohydrate species were present. An aliquot of the de-acidified glycan pool was prepared on a matrix of 3.5-dihydroxybenzene. A Matrix-Assisted Laser Desorption Ionisation-Time of Flight (MALDI-TOF) mass spectrum was obtained in positive ion mode (i.e. molecular ion plus sodium). The following ions could be assigned to carbohydrates (FIG. 9).

| Molecular Ion Na |
|---|
| 1929.9 |
| 2292.5 |
| 2660.1 |
| 3019.1 |

4. SUMMARY

The Glycoprotein GS38-IFNβ carries oligosaccharides with the following structural characteristics:

| (i) | Neutral (no acidic substituents): | 10% ± 0.8% | |
|---|---|---|---|
| | Acidic: | 90% ± 0.6% | |
| (ii) | The total desialylated oligosaccharide pool is heterogeneous, with at least 6 distinct structural components present in the total pool. | | |
| (iii) | The MALDI-TOF mass spectrometry data and the RAAM 2000 data can be summarised as follows: | | |

| Mass detected | Composition | Calculated Mass | gu equivalent |
|---|---|---|---|
| 1786.2 | 5Hex, 4HexNAc 1 2AB, Na | 1782 | 11.1 |
| 1929.9 | 5Hex, 1dHex, 4HexNAc, 1 2AB, Na | 1928 | 12.2 |
| 2295.5 | 6Hex, 1dHex, 5HexNAc 1 2AB, Na | 2293 | 14.5 |
| 2660.1 | 7Hex, 1dHex, 6HexNAc 1 2AB, Na | 2658 | 17.6 |

-continued

| 3019.1 | 8Hex, 1dHex, 7HexNAc, 1 2AB, Na | 3023 | 20.7 |

Hex = Hexose, dHex = deoxyHexose, HexNAc = N-Acetylhexosamine, 2AB = 2-aminobenzamide, Na = sodium ion.

NB. The peak which elutes at 1.0 gu will be included in the matrix in MALDI-TOF mass spectrum and is therefore not detected.

EXAMPLE 7

Expression of human erythropoietin in CHO cells using pMMTC cDNA encoding human erythropoietin (EPO) was derived by PCR with pfu polymerase using human kidney mRNA that had been reverse transcribed. The nucleotide sequence of the 5' and 3' PCR primers are as follows:

5'PCR Primer:

5'GTGGATCCGCCGCCACC/ATG/GGG/GTG/CAC/GAA/TGT/CCT/GCC/TG-3' (SEQ ID NO:4, the CCGC-CGCCACC sequence (SEQ ID NO:5) before the ATG initiation Met codon was designed for optimal translation of the resulting mRNA); and 3'PCR Primer:

5'-GATCTAGACAGTTCTTGTCAATGAGGTTGAAG-3' (SEQ ID NO:6)

The PCR product was gel-purified, cut with restriction enzymes BamHI and XbaI, and then ligated into pGEM-11Z plasmid that has been cut with BamHI and XbaI. After confirming the nucleotide sequence of the EPO coding region, the cDNA was retrieved from pGEM-11Z plasmid by cutting with XhoI and NotI. The EPO cDNA was gel-purified, and inserted into the XhoI-NotI sites of pMMTC, giving rise to a plasmid referred to pMMTC/EPO.

Wild type CHO cells (CHO-K1) were transfected with pMMTC/EPO and initially selected with G-418 for 7 days and then with gradually increased concentrations of Cadmium (4, 8, 16, 32, 64 and 92 $\mu$M). About a few thousand colonies were obtained after the initial G418 selection. When the Cadmium concentration was 64 $\mu$M, about 100 colonies remained viable. Among these 100 colonies, 60 were individually isolated and expanded, and assayed for the levels of EPO in their culture media by Western blot, resulting in identification of 8 high expressing colonies (referred to as E15/1, E15/3, E15/8, E15/10, E15/13. E15/18, E15/26 and E15/30, respectively).

The remaining colonies were further selected in media with 92 $\mu$M Cadmium and several colonies remained viable after this selection, from which 6 colonies (termed C5, C10, C11, C12, C14 and C15, respectively) were individually isolated and assayed for the levels of EPO expression. The levels of EPO secretion by the 8 high expression colonies after 64 $\mu$M Cadmium selection and the 6 colonies after 92 $\mu$M Cadmium selection were further compared by Western blot.

Cells of the selected colonies were seeded onto 35 mm (in diameter) culture dishes. Upon confluency, 1 ml of culture medium was added to each of them and cultured for 24 hrs. The media were then harvested and 10 $\mu$l of each, together with a control 50 ng of EPO (lane 15) were resolved by SDS PAGE and analyzed by Western blot using the Amersham ECL detection system. The Western blot B shown in FIG. 13.

What is claimed is:

1. A purified human β-interferon having a specific activity of $4.8 \times 10^8$ to $6.4 \times 10^8$ I.U. per mg equivalent of bovine serum albumin protein, wherein 25 to 65% of the oligosaccharides of the carbohydrate moiety of said human β-interferon are tri-antennary oligosaccharides.

2. The purified human β-interferon according to claim 1 wherein when $1.5 \times 10^6$ I.U. of the interferon is injected subcutaneously into the back of a rabbit of about 2 kg:

(a) $\geq 128$ I.U./ml of the interferon is detectable in the serum of the rabbit after 1 hour, and/or (b) $\geq 64$ I.U./ml of the interferon is detectable in the serum of the rabbit after 5 hours.

3. A pharmaceutical composition comprising a pharmaceutically acceptable carrier or diluent and, as an active principle, the human β-interferon as defined in claim 1.

* * * * *